United States Patent [19]
Takahashi

[11] Patent Number: 5,172,225
[45] Date of Patent: Dec. 15, 1992

[54] ENDOSCOPE SYSTEM

[75] Inventor: Yutaka Takahashi, Hachioji, Japan

[73] Assignee: Olympus Optical Co., Ltd., Tokyo, Japan

[21] Appl. No.: 731,244

[22] Filed: Jul. 17, 1991

Related U.S. Application Data

[62] Division of Ser. No. 268,399, Nov. 7, 1988, Pat. No. 5,061,994.

[30] Foreign Application Priority Data

Nov. 25, 1987 [JP] Japan .................. 62-296718
Aug. 11, 1988 [JP] Japan .................. 63-201320

[51] Int. Cl.⁵ .................................. H04N 7/18
[52] U.S. Cl. ........................ 358/98; 358/909; 128/6
[58] Field of Search .............. 358/98, 909; 128/4, 128/6

[56] References Cited

U.S. PATENT DOCUMENTS

| | | | |
|---|---|---|---|
| 4,343,300 | 8/1982 | Hattori | 128/6 |
| 4,654,701 | 3/1987 | Yabe | 358/98 |
| 4,727,417 | 2/1988 | Kanno et al. | 358/98 |
| 4,755,873 | 7/1988 | Kobayashi | 358/98 |
| 4,995,396 | 2/1991 | Inaba | 358/98 |

FOREIGN PATENT DOCUMENTS

| | | | |
|---|---|---|---|
| 0221718 | 9/1989 | Japan | 358/98 |
| 0278244 | 11/1990 | Japan | 358/98 |

Primary Examiner—John K. Peng
Attorney, Agent, or Firm—Armstrong & Kubovcik

[57] ABSTRACT

The endoscope system of the present invention recording an endoscope image has a monitor displaying as a picture image an observed image obtained by the endoscope and a recording apparatus recording the obtained image in a recording medium. The state of the recording medium is sensed by a state sensor and a signal showing the state is output outside.

27 Claims, 19 Drawing Sheets

FIG. 19(b) ▨ REFLECTION FACTOR IS LOW

FIG. 19(c) ▨ REFLECTION FACTOR IS HIGH

FIG. 23
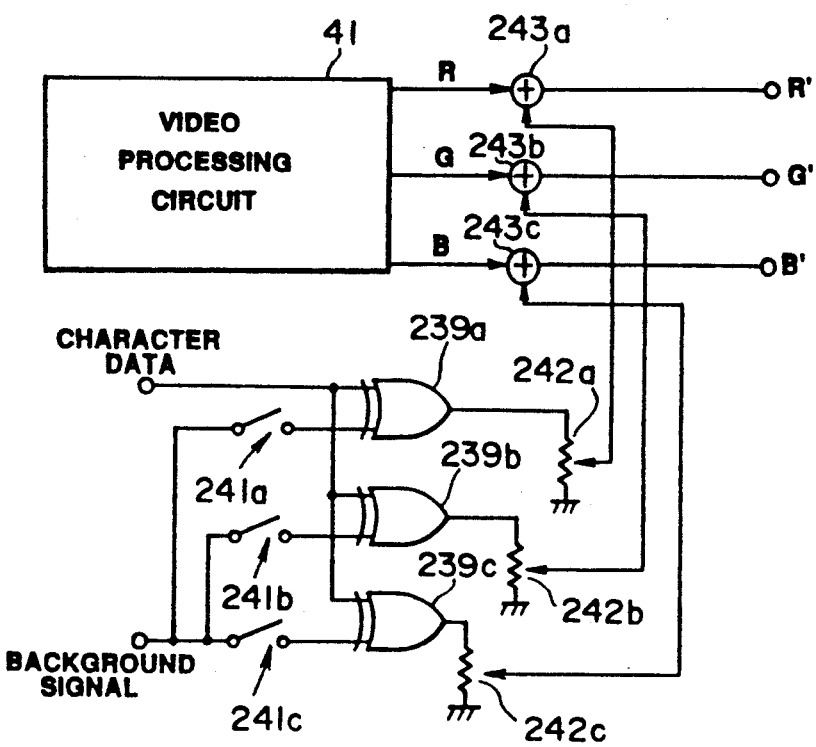
FIG. 25
FIG. 24
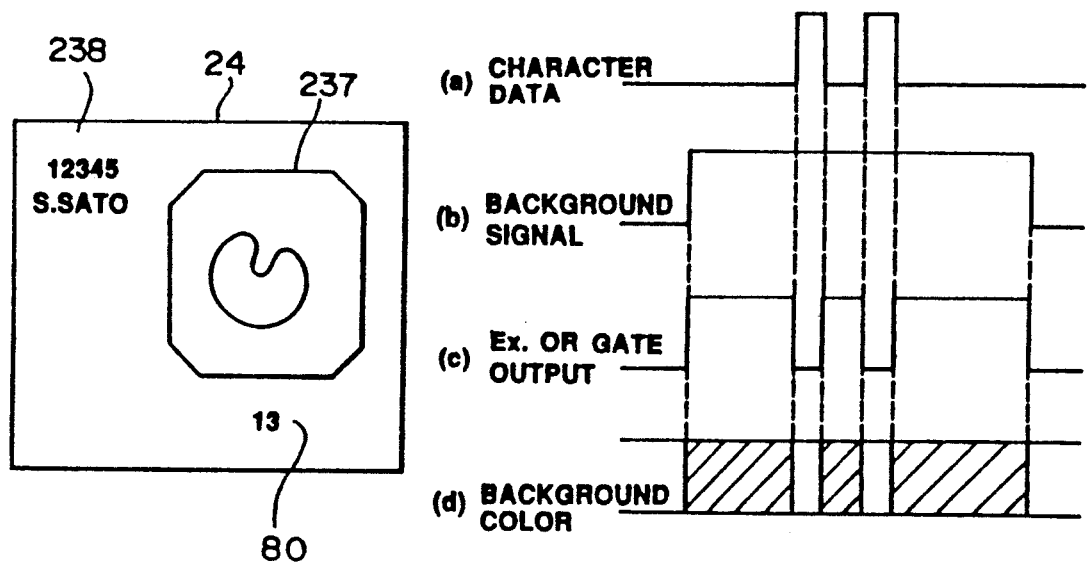

ENDOSCOPE SYSTEM

This is a division, of application Ser. No. 268,399 filed Nov. 7, 1988, allowed May 2, 1991, now U.S.

FIELD OF THE INVENTION

This invention relates to an endoscope system having a detecting function detecting a film exchange in a camera photographing a monitor picture image.

BACKGROUND OF THE INVENTION

Recently, there has come to be extensively used an endoscope (scope or fiber scope) whereby organs within a body cavity can be diagnosed or inspected by inserting an elongate insertable part into the body cavity.

It is used not only for medical uses but also for industrial uses to observe or inspect an object within a boiler, machine or chemical plant pipe.

Further, various kinds of electronic scopes using such solid state imaging device as a charge coupled device (CCD) for the imaging means are also used. Such electronic scope has advantages that the resolution is higher than in a fiber scope, that it is easier to record and reproduce a picture image and further that such picture image processing as the magnification of a Picture image or comparison of two pictures is easier.

Conventionally, in recording the picture image of the above mentioned electronic scope, while seeing the TV monitor, the observer pushes a remote releasing switch of a camera fitted to a TV photographing apparatus as a recording apparatus provided separately from this TV monitor or sends a releasing signal to this camera for photographing. The formation of an electronic scope as described in this related art is shown in FIG. 1.

In FIG. 1, in an electronic scope 1, an elongate insertable part 2 is inserted into a body cavity so that an illuminating light emitted from a light source lamp 6 forming a light source part 4 provided within a control apparatus 3 may be radiated into the body cavity. The image of the observed part radiated with this illuminating light is converted to a picture image signal by a solid state imaging device and not illustrated—provided the tip of the insertable part 2, is then input into a video signal processing circuit 7 provided within the control apparatus 3, is converted to such composite video signal as, for example, of an NTSC system and is input into a character superimposing circuit 8.

On the other hand, the above mentioned control apparatus 3 is provided with a releasing switch 9 and resetting switch 11 which can input and respectively—a releasing signal and resetting signal into an operating circuit 12. When the resetting signal is input into this operating circuit 12, the character superimposing circuit 8 will be instructed to superimpose the number of film frames of 0 on the video signal and thereby a frame number display 14 displayed, for example, below the picture surface together with the picture image of the observed paart in the monitor 13 will be reset to 0. When the releasing signal is input, the operating circuit 12 will output the releasing signal to a camera 17 provided with a photographing apparatus body 16 and a picture image of a monitor not illustrated provided within the photographing apparatus body 16 will be photographed. Simultaneously with this photographing, the operating circuit 12 increases the film counter number value by one (that is, as 1), 1 is superimposed on the video signal in the character superimposing circuit 8 and the film frame number display 14 of the monitor 13 displays 1 of the photographing number. Then, whenever a releasing signal is input, the same operation will be made and the film frame number display 14 will increase. If the film set in the camera 17 is, for example, of 36 frames, when the frame number display 14 becomes 36, the film will be exchanged. When this film exchange ends, the resetting switch 11 will be pushed to reset the film frame number display 14 of the monitor 13 to be 36 and display 0.

Thus, in the endoscope system of the above mentioned related art, whenever the film is exchanged, the resetting switch will have to be pushed and the film frame number display 14 will have to be made 0. However, the photographing apparatus body 16 is lower in the operating frequency than in the control apparatus 3 operated frequently by the operator and is therefore arranged away from the operator so as not to be in the way of the operator. Therefore, after exchanging the film on the photographing apparatus body 16 side, the operator will often forget to push the resetting switch 11 on the control apparatus 3 side. Thereafter, during the operation, though the film has not been finished, such mis-operation as exchanging the film has often occurred.

By the way, in the publication of Japanese Utility Model Application Laid Open No. 58448/1987 (U.S. patent application No. 907833) as a related art, there is shown a technique wherein a sensor sensing the on-off state of the current source of a TV monitor is provided and the release of the camera photographing the TV monitor is operatively connected with this sensor so as to be operatable only when the current source of the TV monitor is on.

Also, in U.S. Pat. No. 4629300, there is shown a picture image photographing apparatus whereby a film photographing a picture image of a TV monitor can be fed in the direction vertical to the film.

OBJECT AND SUMMARY OF THE INVENTION

An object of the present invention is to provide an endoscope system wherein the state of a photographing apparatus ca be known on the observing monitor side by sensing the state of a recording medium, the mis-operation of the photographing apparatus can be prevented and the operatability is high.

The present invention has a displaying means displaying as a picture image an observed image obtained by an endoscope and a recording means recording in a recording medium the picture image displayed by the above mentioned displaying means. The state of the recording medium is detected by a recording medium state sensing means outputting a signal representing the state of the recording medium.

The other features and advantages of the present invention will become apparent enough with the following explanation.

BRIEF DESCRIPTION OF THE DRAWINGS

FIG. 2 is a general explanatory view of an endoscope system.

FIG. 3 is a block diagram explaining the formation of a video processing circuit of a mosaic system.

FIG. 4 is an explanatory view of a camera controlling part.

FIG. 5 is an explanatory view of a camera controlling part.

FIGS. 6 to 9 are plan views showing respectively the operating orders of a mechanism part detecting a winding operation.

FIG. 10 is an explanatory view of a camera controlling part.

FIG. 11 is an explanatory view of an encoder disc.

FIG. 14 is an explanatory view of an endoscope system wherein the imaging system is of a frame sequential system.

FIG. 15 is a block diagram explaining the formation of a video processing circuit of a frame sequential system.

FIGS. 18 to 20 relate to the ninth embodiment of the present invention.

FIG. 18 is an explanatory view of an endoscope system sensing the kind of the film.

FIGS. 19A-19C show an explanatory view of a cartridge.

FIG. 20 is an explanatory view of a photosensor.

FIGS. 22 to 25 relate to the 11th embodiment of the present invention.

FIG. 22 is an explanatory view of an endoscope having an outside input apparatus.

FIG. 23 is a circuit diagram of a character superimposing circuit.

FIG. 24 is a timing chart view explaining the operation of a character superimposition.

FIG. 25 is an explanatory view of a displayed picture image of an observing monitor.

DETAILED DESCRIPTION OF PREFERRED EMBODIMENTS

The embodiments of the present invention shall be concretely explained in the following with reference to the drawings.

Figure 1:
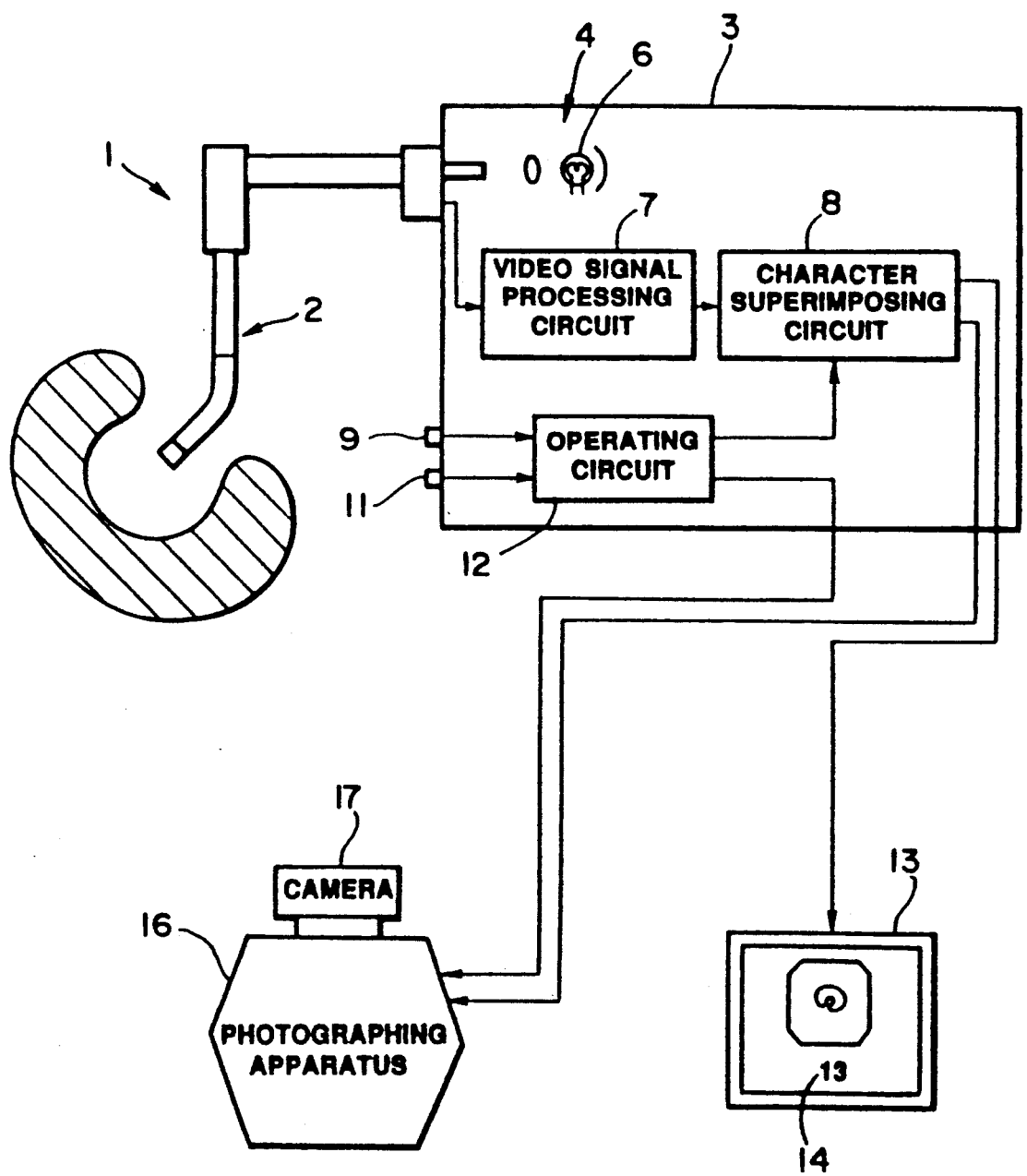
FIG. 1 is a general explanatory view of an endoscope system as a related art.
Figure 2:
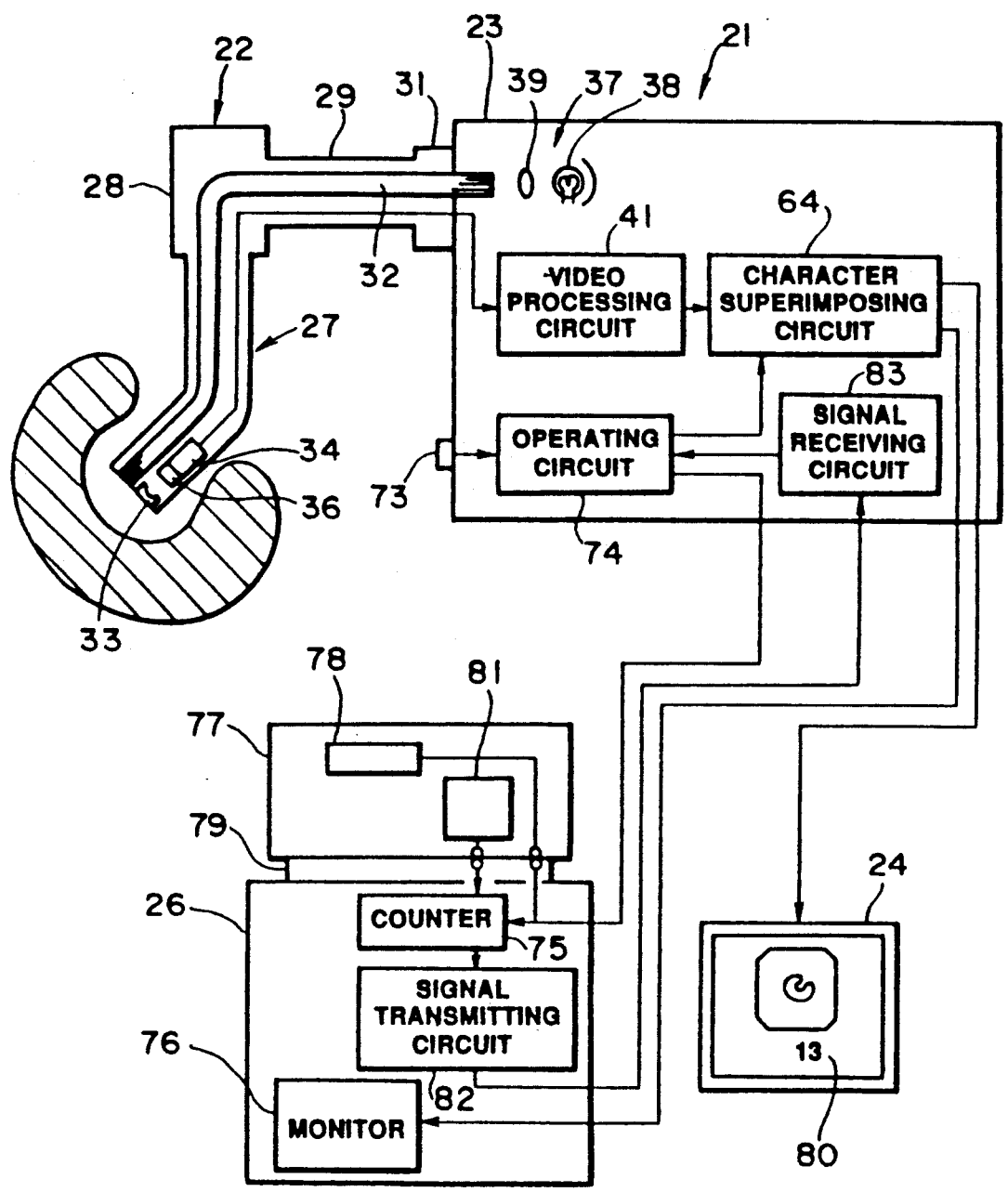
FIGS. 2 to 4 relate to the first embodiment of the present invention.
Figure 3:
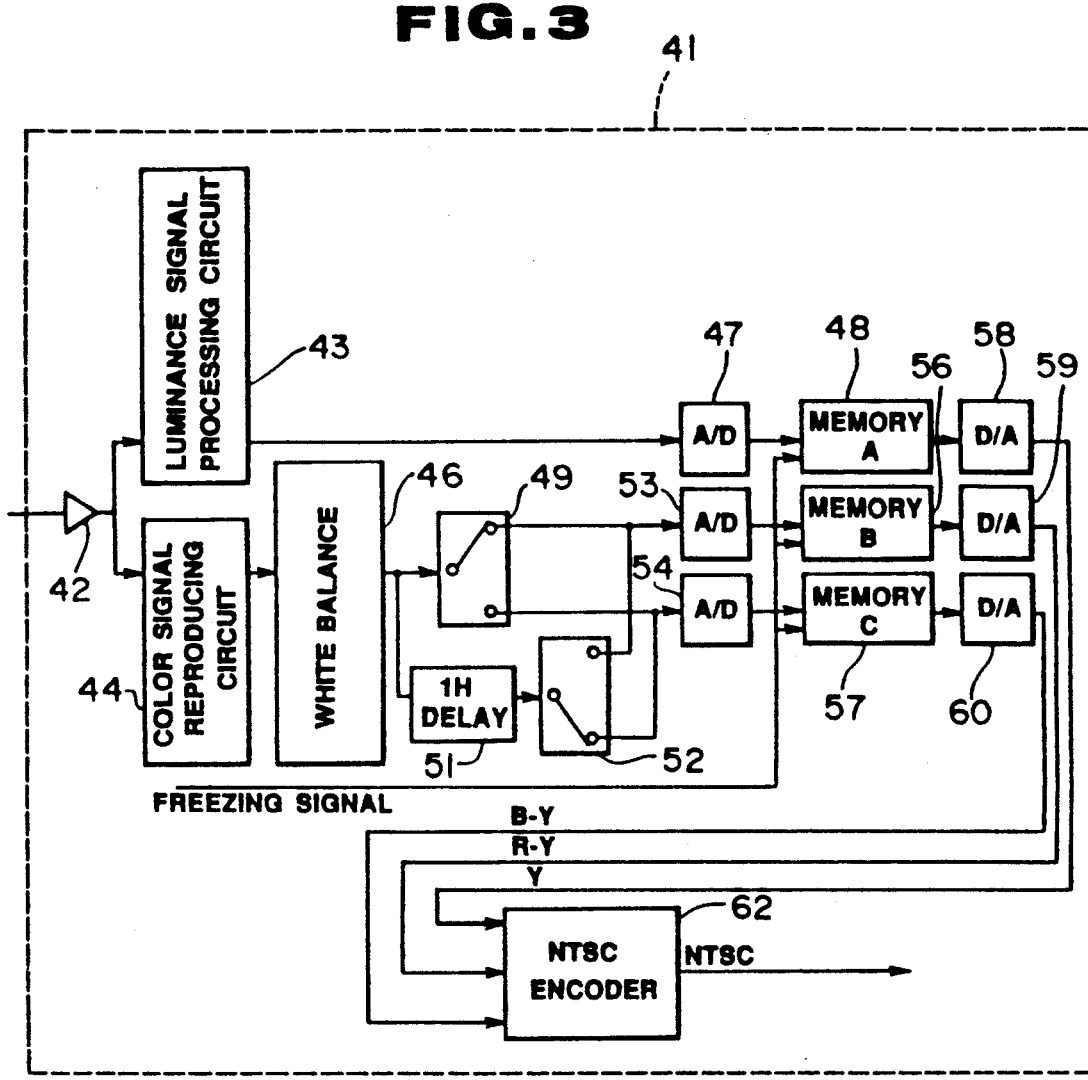
Figure 4:
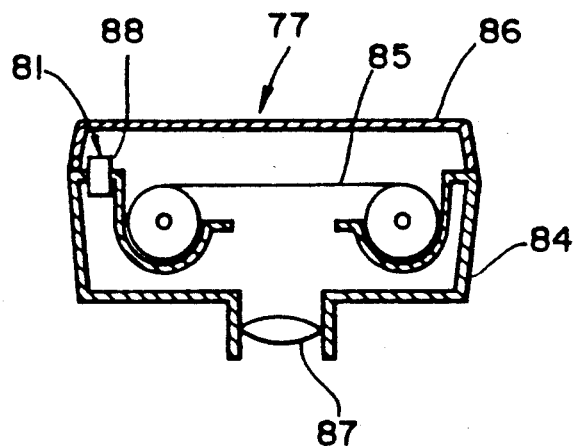

FIGS. 2 to 4 show the first embodiment of the present invention.

In FIG. 2, an endoscope system 21 comprises an electronic scope 22 as an imaging means of an imaging system of a mosaic type, a control apparatus 23 as a signal processing means connected with this electronic scope 22, an observing monitor 24 which can display an observed picture image obtained by the electronic scope 22 and a photographing apparatus body 26 as a recording means.

The above mentioned electronic scope 22 comprises an elongate flexible insertable part 27, a thick operating part 28 connected to this insertable part at the rear end and a light guide and signal cable 29 extended out of this operating part 28 on the side part. Further, this light guide and signal cable 29 is provided at the tip with a light guide and signal connector 31 connected to the above mentioned control apparatus 23.

The above mentioned insertable part 27 is provided at the tip with a light guide 32 on the exit end surface. This light guide 32 is inserted through the insertable part 27, operating part 28 and light guide and signal cable 29 and is led to the light guide and signal connector 31 provided at the tip with the light guide on the entrance surface. An illuminating light emitted from a light source 38 forming a light source part 37 provided within the control apparatus 23 is condensed by a condenser lens 39 and enters this light guide 32 on the entrance end surface. The insertable part 27 is provided at the tip with an objective lens 33. A solid state imaging device 34 to which is pasted a color filter array 36 provided in the form of a mosaic with color separating filters transmitting respective colors, for example, of R(red), G(green) and B(blue) is provided on the imaging surface in the image forming position of this objective lens 33. This solid state imaging device 34 photoelectrically converts the formed image to an electric signal and outputs this electric signal to a video processing circuit 41 provided within the control apparatus 23 through the insertable part 27, operating part 28, light guide and signal cable 29 and light guide and signal connector 31.

In FIG. 3, the electric signal is input and amplified in a pre-amplifier 42 forming a video processing circuit 41 and is input into a luminance signal processing circuit 43 and color reproducing circuit 44. A luminance signal Y is produced from the luminance signal processing circuit 43. Color difference signals R-Y and B-Y are produced on each horizontal line in time series from the color signal reproducing circuit 44 and are compensated for the white balance in a white balancing circuit 46. The luminance signal Y output form the luminance signal processing circuit 43 is digitalized by an A/D conveter 47 and will be memorized in a memory A 48. The output of the white balancing circuit 46 is branched, one branch is input into an analogue switch 49 and the other is delayed by one horizontal line by a 1H delay line 51 and is input into an analog switch 52. These analog switches 49 and 52 are switched by a switching signal of a timing generator and not illustrated—to produce the color difference signals R-Y and B-Y. These color difference signals R-Y and B-Y are digitalized by A/D converters 53 and 54 and are memorized in memories B 56 and C 57. The luminance signal Y and color difference signals R-Y and BOY memorized in the memories A 48, B 56 and C 57 are analogized respectively by the D/A converters 58, 59 and 60, are input into an NTSC encoder 62 to a composite video signal of an NTSC system which is input into a character superimposing circuit 64.

On the other hand, the above mentioned control apparatus 23 is provided with a releasing switch 73 connected so as to be able to input a releasing signal into an operating circuit 74 formed, for example, of a CPU and connected so as to be able to output the releasing signal to a counter 75 as a counting means provided within the above mentioned photographing apparatus body 26 and a camera controlling part 78 having a shutter and film winding mechanism contained in a camera 77 provided in a camera 77 provided through an adapater 79 on the photographing apparatus body 26.

The above mentioned character superimposing circuit 64 is connected with the above mentioned operating circuit 74 so as to superimpose the number of film frames on the composite video signal. This character superimposing circuit 64 outputs a composite video signal on which the number of film frames has been susuperimposed to the above mentioned monitor 24 and a photographing monitor 76 provided in the above mentioned photographing apparatus body 26 so as to be able to respectively display the observed picture image having the film number display 80.

The above mentioned counter 75 is connected so as to be able to increase the counted numerical value by on when the releasing signal is input and to output to a signal transmitting circuit 82 the counted numerical value increased by one. This counter 75 is connected with a film exchange detector 81 as a recording medium state sensing means so as to be able to input a film exchanging signal from the film exchange detector 81.

The above mentioned signal transmitting circuit 82 is connected so as to be able to output a counted numerical value to a signal receiving circuit 83 provided within the above mentioned control apparatus 23. Further, this signal receiving circuit 83 is connected to the above mentioned operating circuit 74 so as to be able to input the counted numerical value into the operating circuit 74.

In FIG. 4, the above mentioned camera 77 is formed of a camera body 84 and a back lid 86. This camera body 84 is fitted in the image forming position with a film 85 and is provided with a lens system 87.

The above mentioned camera body 84 is provided, for example, with a reflecting type photosensor 88 (infrared ray type) so as to face the above mentioned back lid 86. In case the back lid 86 is closed, this reflecting type photosensor 88 will again input the infrared rays reflected by the back lid 86 into a phototransistor of the reflecting type photosensor 88. In case the back lid 86 is opened to exchange the film, the reflected light will no longer enter the above mentioned phototransistor and therefore the film exchange will be able to be detected.

Now, the operation of the endoscope system formed as mentioned above shall be explained.

The insertable part 27 of the electronic scope 22 is inserted within a body cavity. An illuminating light illuminating the body cavity interior 59 is emitted out of the exit end surface of the light guide 32 provided at the tip of this insertable part 27. The image of the illuminated observed part is transmitted through the color filter array 36 and is formed on the solid state imaging device 34. The formed image is photoelectrically converted to a picture image signal which is input into the video processing circuit 41. The picture image signal is converted by this video processing circuit 41 to such composite video signal as, for example, of an NTSC system which is output to the observing monitor 24 and photographing monitor 76 through the character superimposing circuit 64.

Here, if the releasing switch 73 provided in the control apparatus 23 is pushed, a releasing signal will be input into the operating circuit 74 which will output this releasing signal to the counter 75 and camera controlling part 78 which will open and close the shutter and wind up the film 85 by the releasing signal. The counter 75 increases the counted numerical value by one by the releasing signal and outputs the counted numerical value to the signal transmitting circuit 82 which outputs the counted numerical value to the signal receiving circuit 83 within the control apparatus 23. Further, this signal receiving circuit 83 inputs the counted numerical value into the operating circuit 74 which outputs this input counted numerical value to the character superimposing circuit 72 which superimposes the counted numerical value, that is, the number of film frames on the composite video signal and outputs the composite video signal to the observing monitor 24 and the monitor 76 provided in the photographing apparatus body 26 so as to display on the picture surface the observed image having the film frame number display 80.

Further, whenever the releasing switch 73 is pushed to photograph the observed picture image, the above mentioned operation will be repeated. When the photographing with the film 85 ends and the back lid 86 of the camera 77 is opened to exchange the film 85, as mentioned above, the film exchange will be detected by the film exchange detector 81 and this film exchanging signal will be output to the counter 75 which, when this film exchanging signal is input, will reset the counted numerical value at 0 and will input this counted numerical value into the operating circuit 74 through the signal transmitting circuit 83. The operating circuit 74 outputs the counted numerical value to the character superimposing circuit 72. This character superimposing circuit 72 superimposes 0 of the counted numerical value on the composite video signal and outputs the composite video signal to the observing monitor 24 and photographing monitor 76. The observed picture image on which the counted numerical value, that is, 0 of the number of film frames has been superimposed is displayed on the picture surfaces of the observing monitor 24 and photographing monitor 76.

By the formation as described in this embodiment, as the film exchange is detected and the film frame number display 80 is automatically reset on the observing monitor 24, there will be no necessity of manually resetting the film frame number whenever the film is exchanged, no exchanging the film 85 before it ends and no photographing though the film 85 ends.

By the way, the releasing switch 73 may be provided in the electronic scope 22 or photograpahing apparatus body 26. Further, the counter 75 may be provided in the control apparatus 23 or adapter 79. Also, the signal transmitting circuit 82 may be provided in the camera 77 or adapter 79.

By the way, in the case of photographing with a freezing circuit provided within the video processing circuit 41, the picture image may be a still picture.

Further, in case the film ends and the counter 75 shows a predetermined number of frames, the releasing signal from the releasing switch 73 may be prohibited from being input into the operating circuit 74. While the signal during the film exchange is being output to the operating circuit 74 from the film exchange detector 81, the release may be prohibited by the operating circuit 74.

Further, in case the film is of 20 frames, when five frames remain, the film frame number signal output from the operating circuit 74 may be delivered as a flickering signal to the character superimposing circuit 64 so as to flicker the film frame number display 80 of the observing monitor 24. In such case, frame numbers of 16 to 20 will flicker on the observing monitor 24. By the way, not only the remaining five frames but also any number of frames may be made to flicker. The color of be frame number not flickered may the changed or the frame number may be enclosed with a frame which may be made to flicker.

Figure 5:
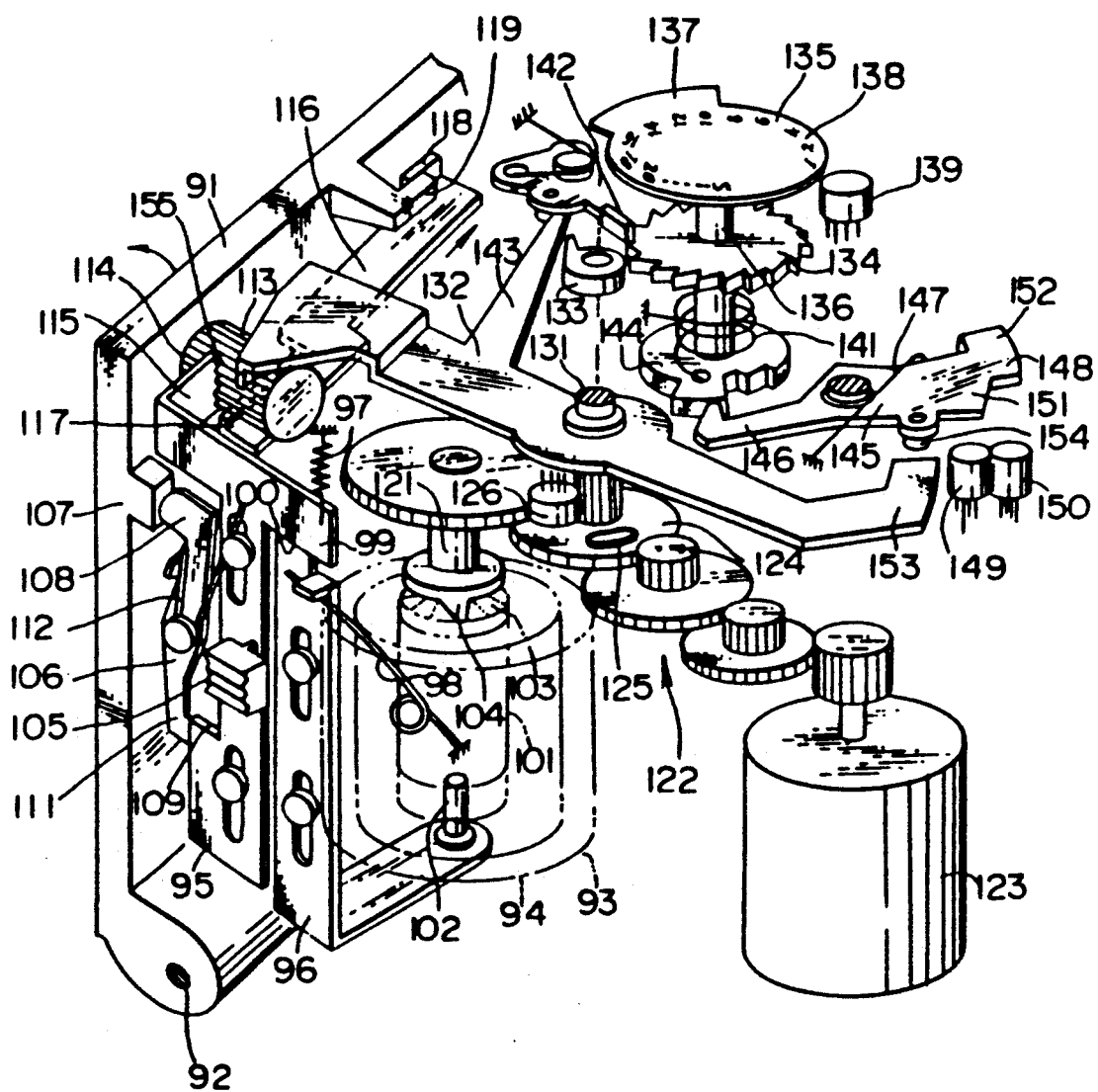
FIGS. 5 to 9 relate to the second embodiment of the present invention.

FIG. 5 shows the second embodiment of the present invention.

In this embodiment, the camera controlling part and film exchange detector described in the first embodiment are made integral.

The parts other than the camera controlling part and film exchange detector are the same as in the first embodiment.

In FIG. 5, the reference numeral 91 represents a back lid provided in an aperture of a cassette housing chamber and pivoted at the lower end to a pivotal shaft 92 provided in the camera body 84 so as to open and close the aperture of the cassette housing chamber. A sliding plate 95 moving in the vertical direction is provided on the side adjacent to a film winding part 94 of a film cassette 93. Also, an engaging operating lever 96—as an engaging operating member moving parallel with this sliding plate 95—is provided. The sliding plate 95 is energized to be pushed upward by a tension coil spring 97 and the engaging operating lever 96 is energized to be pushed upward by a twisted spring 98. A projecting piece 99 is formed integrally on the upper side of the sliding plate 95. The engaging operating lever 96 contacts at the upper end with a butting surface 100 made of the lower end surface of this projecting piece 99 so as to be regulated in the position and is bent and extended at the lower end toward the lower side of the film winding part 94 of the film cassette 93. A push-up pin 102 to push up an inner cylinder 101 of the film winding part 94 is provided at this extended tip. Engaging pawls 103 exposed on the upper surface of the film cassette 93 are provided at the upper end of the inner cylinder 101 so as to contact and engage with a later described winding pawl 104 when the inner cylinder 101 is pushed up. The above mentioned sliding plate 95 is provided with a back lid opening knob 105 exposed out of the camera body so as to be pushed down by using this knob 105. The above mentionend back lid 91 opens as operatively connected with the fall of this sliding plate so as to open the aperture of the cassette housing chamber. A locking lever 106 is provided between the back lid 91 and sliding plate 95, is provided at the upper end with a butting part 108 butting a projection 107 provided on the back lid 91, has at the lower end a stopper part 111 formed to engage with a stopper end edge 109 formed by incising the sliding plate 95 and is energized by a twisted spring 112 to rotate so that the above mentioned butting part 108 will contact the projection 107 side. When the back lid 91 is closed, the locking lever 106 will be rotated to be in the position in which the projection 197 will contact the butting part 108 and the stopper part 111 will retreat from the stopper end edge 109. When the sliding plate 95 is pushed down, the projection 107 of the back lid 91 will retreat from the locking lever 106, the stopper edge 109 will fall, therefore, the locking lever 106 will be rotated by the twisted spring 112, the stopper part 111 will be engaged in contact with the above mentioned stopper end edge 109 and the sliding plate 95 will be prevented from rising and returning. When the back lid 91 is closed, the projection 107 will push the butting part 108 and therefore the locking lever 106 will rotate to release the above mentioned engagement. Therefore, the sliding plate 95 automatically rises and returns due to the energizing force of the tension coil spring 97. By the way, in response to the rising and falling operation of the above mentioned sliding plate 95, the engaging operating lever 96 moves to raise and lower the above mentioned inner cylinder 101. The above mentioned sliding plate 95 is provided at the upper end with a projecting piece part 115 forming a rack gear 114 engaged with a transmitting gear 113. A rack gear 117 formed at one end of a back lid closing sliding plate 116 is engaged with the above mentioned transmitting gear 113 so that, when this transmitting gear 113 rotates, the above mentioned sliding plate 116 will move parallel with the back lid 91. An engaging piece 118 is formed at the other end of the back lid closing sliding plate 116 so as to be engageable with an engaging pawl 119 provided on the back lid 91, that is, to be disengageable when the above mentioned back lid closing sliding plate 116 rotates in the direction indicated by the arrow due to the rotation of the transmitting gear 113 as accompanying the fall of the above mentioned sliding plate 95 and to be engageable when the sliding plate 116 moves and returns in the reverse direction.

On the other hand, a winding shaft 121 having the above mentioned winding pawl 104 is connected to a winding motor 123 through a gear train 122 consisting of a plurality of spur gears so that the rotation of the above mentioned winding motor 123 will be received as reduced in the speed by the gear train 122 and the winding part 94 of the film cassette 93 will be driven for winding up. A gear 124 among the intermediate gears of the above mentioned gear train 122 is formed to make one rotation in response to the feed of one frame and has a slot 125 made in the peripheral part. A photocoupler 126 as a detector is set in a position corresponding to an orbit through which the slot 125 will pass when the gear 124 rotates so that, by detecting the above mentioned slot 125, it will be sensed that the gear 124 has made one rotation and the rotation of a winding motor 123 will be stopped.

On the other hand, a shaft 131 of the above mentioned gear 124 is extended upward. A resetting lever 132 is inversely fitted in the intermediate part to this shaft 131 in the intermediate part so as to be freely rotatable. Further, a frame feeding pawl 133 is fitted and fixed to the above mentioned shaft 131 at the upper end so that a frame counting ratchet wheel 134 may be rotated by this frame feeding pawl 133. The above mentioned frame counter is formed as follows. That is to say, the ratched wheel 134 is fitted and fixed to a shaft 136 of a frame counting plate 135 so as to be rotated by one tooth to rotate the frame counting plate 135 by one frame graduation. The above mentioned frame counting plate 135 is formed to be like a circular plate A large diameter projecting part 137 and as a detected part—is formed in response to the frame number graduation for more than, for example, 16 frames so that, when the figure of the frame number graduation 138 becomes higher than 16, this large diameter projecting part 137 will be detected as opposed to a first photocoupler 139 for sensing a remaining number alarm. When this first photocoupler 139 detects the above mentioned large diameter projecting part 137, by utilizing this signal, for example, a displaying lamp provided within a finder of the camera body 84 will be controlled to flicker to inform that the remaining frames are few.

An energizing coil spring 141 is wound on the shaft 136 of the above mentioned frame counting plate 135 so as to energize the above mentioned frame counting plate 135 and shaft 136 in the direction of rotating clockwise. Further, a reverse rotation preventing engaging pawl 142 is engaged with the above mentioned ratchet wheel 134 to prevent the reverse rotation of the ratchet wheel 134. By the way, the above mentioned engaging pawl 142 is to be released by a releasing arm 143 formed to project on the resetting lever 132.

Figure 6:
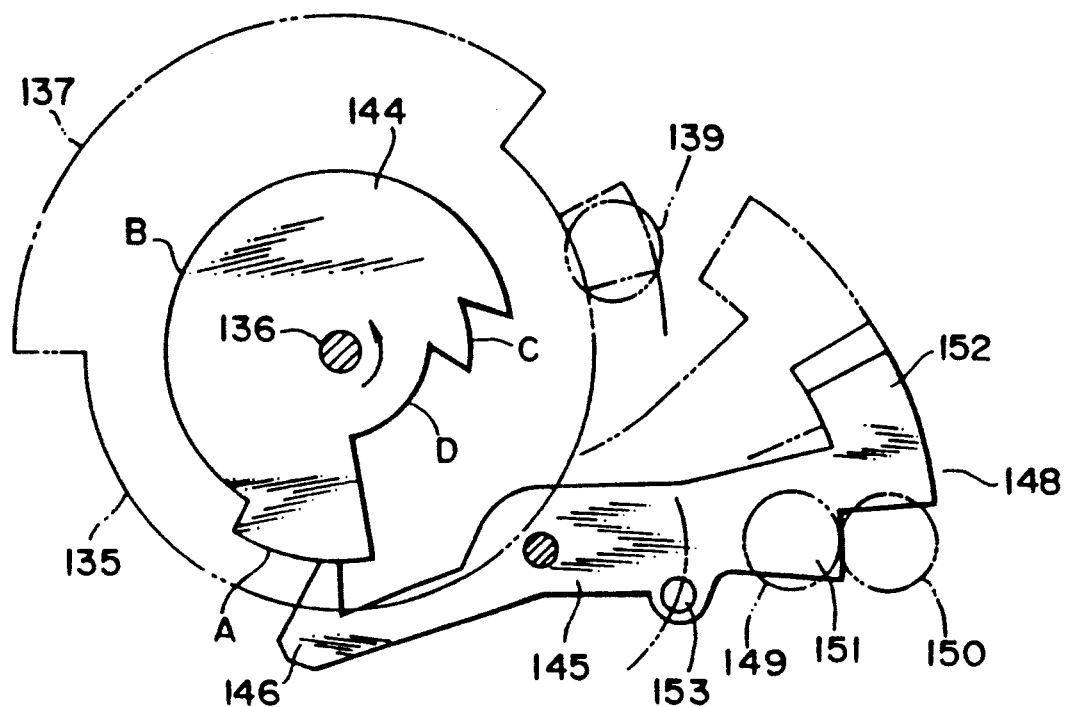

A discriminating cam 144 is fitted and fixed to the lower end of the shaft 136 of the above mentioned frame counting plate 135 and is formed as shown in FIG. 6. That is to say, the first cam surface A corresponding to the leader part of the film, the second cam surface B corresponding to the part until 20 frames, the third cam surface C corresponding to the trailer part and the fourth cam surface D corresponding to the end are formed in the order of the rotating direction and to be smaller in the diameter in turn. The cam follower part 146 of a cam lever 145 elastically contacts the peripheral surface of this cam 144.

Figure 7:
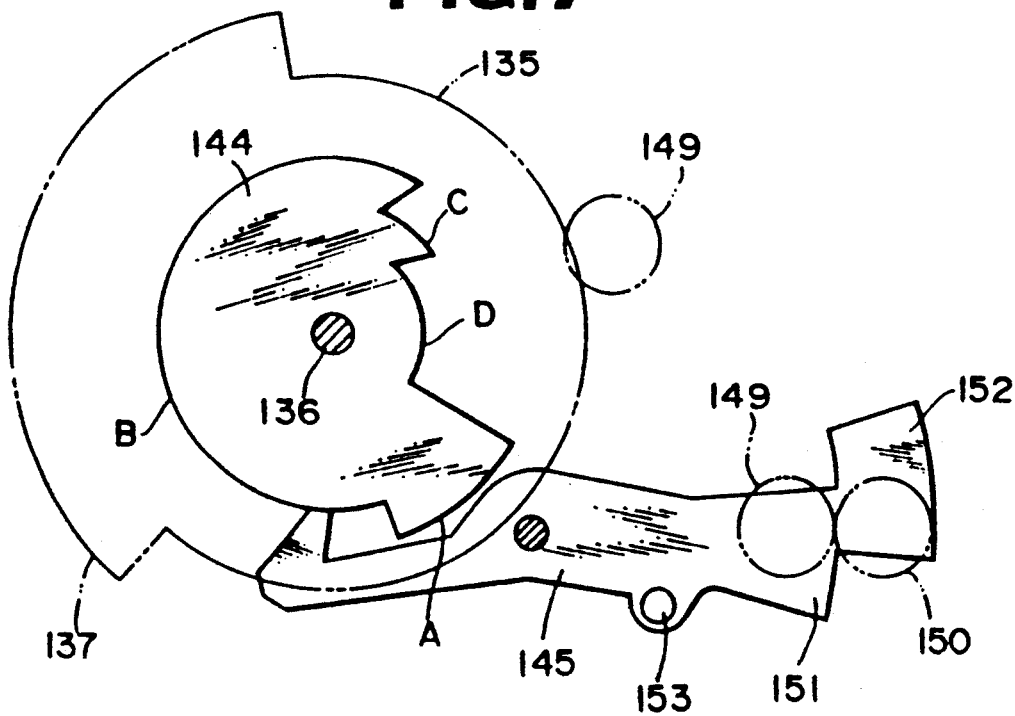

The above mentioned cam lever 145 is pivoted in the intermediate part and is energized by a twisted spring 147 so that the above mentioned follower part 146 may follow in contact with the peripheral surface of the above mentioned cam 144. A sensed part 148 is formed at the other end of the cam 145 so as to be optically sensed by the second and third photocouplers 149 and 150 as a pair of sensors set as arranged on a straight line passing through the rotation center of the cam lever 145. That is to say, the above mentioned sensed part 148 is made by forming a pair of plate parts 151 and 152 deviated from each other on the right and left and the second plate part 152 on the tip side is deviated as advanced in the rotating direction of the cam lever 145 more than the first plate part 151 on the lid end side. The state that, when one of the plate parts 151 and 152 is opposed to one of the corresponding photocouplers 149 and 150, the other plate part 151 or 152 will not be opposed to the other photocoupler 149 or 150 (FIGS. 6 and 8) or the photocouplers 149 and 150 will be opposed to both plate parts 151 and 152 (FIG. 7) can be selected. Further, the cam lever 145 is provided with a pin 154 receiving the resetting lever 132 at the resetting operation end 153 so that, by the resetting lever 132, against the energizing force of the twisted spring 147, the cam lever 145 may be rotated and may be retreated to the position shown by the two-point chain lines in FIG. 6.

The above mentioned resetting lever 132 is provided at the other end with a rack 155 engaging with the above mentioned transmitting gear 113 so as to be slid by the rotation of the transmitting gear 113.

The above mentioned first to third photocouplers 139, 149 and 150 are to deliver output signals to the film exchange detector described in the first embodiment so that the exchange of the film 85 may be sensed.

The operation of the above mentioned film winding apparatus shall be explained in the following. First of all, in the case of containing the film cassette 93 in the cassette containing chamber, the sliding plate 95 is pushed down by the back lid opening knob 105. As operatively connected with it, the back lid 91 opens, the locking lever 106 rotates and its stopper part 111 drops into and engages with the stopper end edge 109 to prevent the rise and return of the sliding plate 95. With the fall of the above mentioned sliding plate 95, the transmitting gear 113 is rotated by the rack gear 114 and the back lid closing sliding plate 116 is moved to disengage the engaging piece 113. Therefore, the back lid 91 can open as described above. Further, with the fall of the sliding plate 95, the engaging operating lever 96 in contact with the butting surface 100 also falls and the push-up pin 102 submerges and retreats in the bottom of the cassette containing chamber. When the above mentioned transmitting gear 113 rotates, the resetting lever 132 will also rotate, the engaging pawl 142 will be rotated and separated from the ratchet wheel 134 by the releasing arm 143 and the cam lever 145 will be rotated to the position indicated by the two-point chain lines in FIG. 6 by the resetting operating end 153 (the cam lever 145 will perfectly separate from the peripheral surface of the discriminating cam 144). Thus, the above mentioned ratchet wheel 134 is released. Therefore, by the energizing coil spring 141, the frame counting plate 135 and discriminating cam 144 are rotated to return to the standing-by position indicated by the solid lines in FIG. 6. All the first to third photocuplers 139, 149 and 150 are in the non-sensing state and a combination signal of ① in the table is obtained. This signal is output to the film exchange detector 81.

| | Sensing states | | | | |
|---|---|---|---|---|---|
| | ① | ② | ③ | ④ | ⑤ |
| First photocoupler | 0 | 0 | 0-15 0 | 16-a 1 | 1 1 |
| Second photocoupler | 0 | 1 | | 1 | 0 0 |
| Third photocoupler | 0 (A) | 0 (B) | | 1 (C) | 0 (D) 0 (E) |

(A) Back lid opened.
(B) Leader part fed.
(C) 20 frames.
(D) Trailer part fed.
(E) End.

On the other hand, when the cassette containing chamber is fitted with the film cassette 93 and the back lid 91 is closed, the projection 107 will contact the butting parat 108 to release the sliding plate 95. Therefore, this sliding plate 95 rises and returns to rotate the transmitting gear 113 and, following the butting surface 100, the engaging operating lever 96 rises and returns, pushes up the inner cylinder 101 of the film cassette 93 with its push-up pin 102 and engages the engaging pawl 103 with the winding pawl 104. Now, the engaging pawl 103 and winding pawl 104 may not correctly engage with each other and may butt with each other on the tooth tip surfaces. However, in such a case, the engaging operating lever 96 will not follow while butting on the butting surface 100 of the sliding plate 95 but will remain as it is and will not restrict the movement of the sliding plate 95. That is to say, the back lid 91 is normally closed. Then, as described later, in order to feed the leader part, the winding pawl 104 perfectly engages immediately after the start of the rotation and normally winds up the film.

When the transmitting gear 113 is rotated by the rise of the sliding plate 95, the back lid closing sliding plate 116 will move to engage its engaging piece 118 with the engaging pawl 119 of the back lid 91. That is to say, the back lid 91 is locked as closed. Further, the resetting lever 132 is also rotated clockwise and separates from the engaging pawl 142 and cam lever 145. Therefore, the engaging pawl 142 engages with the ratchet wheel 134 and, as shown in FIG. 6, the cam lever 145 contacts in the cam follower part 146 with the first cam surface A of the discriminating cam 144 and stands by. Thereby, the second photocoupler 149 is opposed to the first plate part 151 to sense it but the second photocoupler 150 is in the non-sensing state. The first photocoupler 139 is also naturally in the non-sensing state. That is to say, the combination signal of ② in the table is obtained. This signal is delivered to the film exchange detector 81. With the change of the combination signal ① to the combination signal ②, the film exchange is sensed and the number of frames integrated in the counter 75 is reset at 0. As described in the first embodiment, this reset frame number is delivered to the operating circuit 74 through the signal transmitting circuit 82 and signal receiving circuit 83.

On the other hand, by the combination signal ② the winding motor 123 is rotated and the leader part feeding operation begins. That is to say, the rotation is transmitted to the winding pawl 104 through the gear train 22 and winding shaft 121 and the inner cylinder 11 is rotated through the engaging pawl 103 engaged with this winding pawl 104.

Thus, the leader part of the film is wound up. The gear 124 in the course of the gear train 122 rotates during the feeding operation. By detecting the number of passages of the slot 125 of the gear 124 with the photocoupler 126, the number of feeds is detected. In this case, when the gear 124 makes one rotation, it will operate by one frame feed. When this frame feed is made, together with the above mentioned gear 124, the frame feeding pawl 133 will rotate through the shaft 131 of the gear 124 to rotate the ratched wheel 134 by one tooth. When this leader part is fed by a predetermined number of frames, for example, by three frames, the discriminating cam 144 will also rotate to be in the state shown in FIG. 7. That is to say, the cam lever 145 so far in contact with the first cam surface A separates from the first cam surface A and now contacts the second cam surface B. Thus, the cam lever 145 also rotates by the lift difference and the first and second plate parts 151 and 152 of the second part 148 are opposed respectively to both of the second and third photocouplers 149 and 150. That is to say, the sensing state of ③ in the above mentioned table is made. As soon as this state is made, the operation of the winding motor 123 will be stopped. Thereafter, whenever a releasing signal is received, the winding motor 123 will automatically operate and the operation of feeding one frame of stopping the feeding operation when the gear 124 makes one rotation and the slot 125 is detected by the photocoupler 126 will be made each time. Thus, when 15 frames are exposed and the 16th frame is fed, the large diameter projecting part 137 will be opposed to the first photocoupler 139 which will be in the detecting state. The displaying lamp within the finder flickers to inform that few frames remain.

Figure 8:
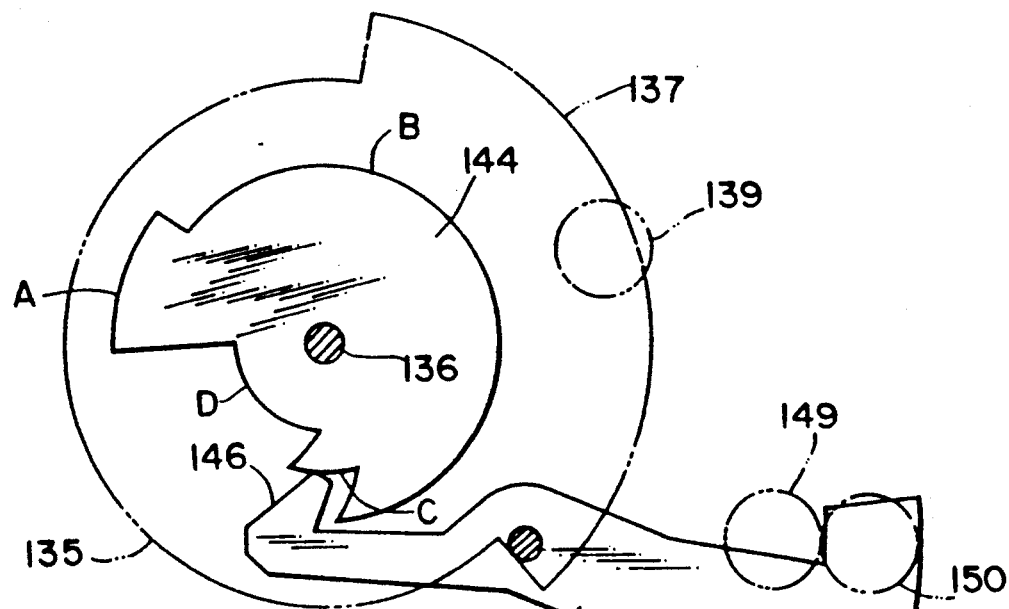
Figure 9:
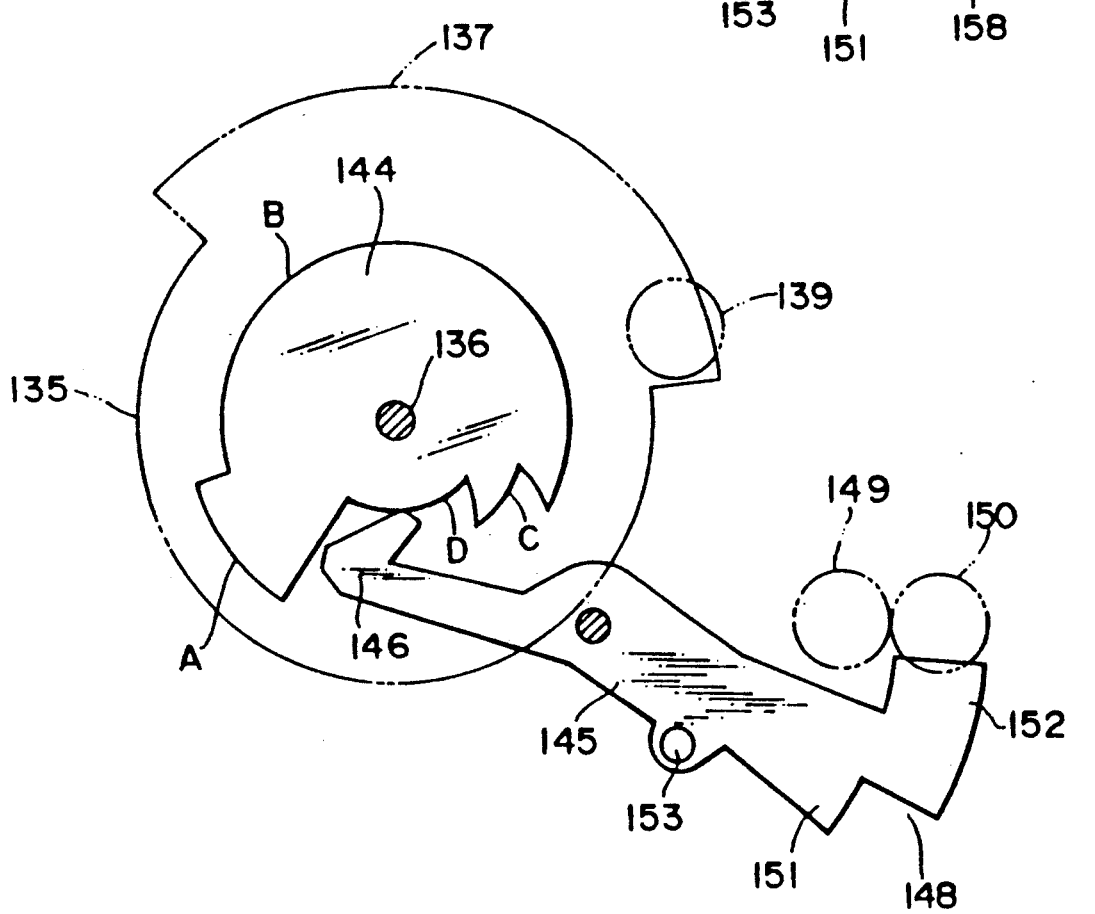

Further, when the photographing is continued and 20 frames are used up, the cam follower part 146 of the cam lever 145 will drop onto the third cam surface C of the discriminating cam 144 and the cam lever 145 will make a fixed rotation to be in the state shown in FIG. 8. Therefore, the first plate part 151 separates from the second photocoupler 149 and the second plate part 151 remains opposed to the third photocoupler 150. Therefore, the sensing state of ④ in the above mentioned table is made. Receiving this signal, the control part operates the winding motor 123 and feeds the trailer part continuing the feed, for example, by three frames. When this trailer part feed is completed, the discriminating cam 144 will make a fixed rotation to drop the cam follower part 146 of the cam lever 145 onto its fourth cam surface D and the cam lever 145 will be in the state in FIG. 9. That is to say, both of the second and third photocouplers 149 and 150 separate from the sensed part 148 to be in the non-sensing state. Further, at this time, the first photocoupler 139 will sense the large diameter projecting part 137 and will be therefore shown in the end state ⑤ in the above mentioned table. This is recognized in the control part.

With the above, one operation is completed. Now, in case the film cassette 93 is to be taken out, as described above, by pushing down the back lid opening knob 105, the back lid 91 is opened and the film cassette 93 is taken out. At this time, as described above, the resetting operation will be made.

Now, such five respective states as are shown in the above mentioned table are discriminaated by the first, second and third photocouplers 139, 149 and 150. By only the second and third photocouplers 149 and 150, both states of ① and ⑤ are of the operation stop and are of the same detection contents. Therefore, substantially, these two photocouplers 149 and 150 are enough. However, in these states as they are, at the time of resetting, the cam lever 145 will move in the reverse direction in the order of ⑤→④→③→②→① and therefore, in the above mentioned states of ④ and ②, the winding motor 123 will move. Therefore, in this invention, the program is set so that, once the end state ⑤ is made, the winding motor 123 will not move until the back lid opens next. In order to discriminate the above mentioned states of ① and ⑤, the large diameter projecting part 137 of the frame counting plate 135 is detected with the first photocoupler 139 to distinguish the respective states.

The other formations and operations are the same as in the first embodiment.

In this embodiment, the camera controlling part and film exchange detector are made integral so that the film exchange may be sensed by the output signals of the first to third photocouplers 139, 149 and 150 forming the camera controlling part. Therefore, as compared with the first embodiment, the formation of the film exchange detector can be made simpler.

Figure 10:
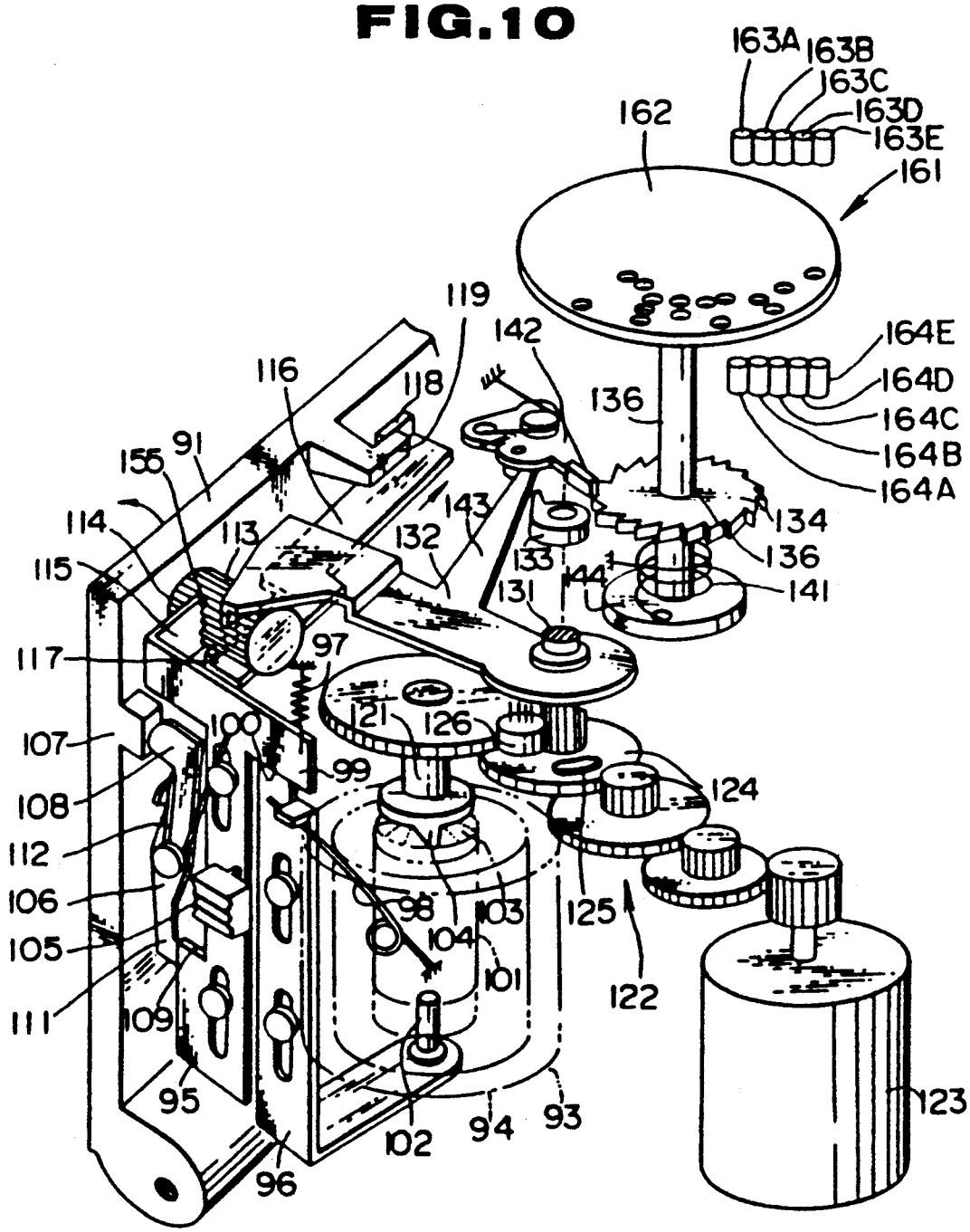
FIGS. 10 and 11 relate to the third embodiment of the present invention.
Figure 11:
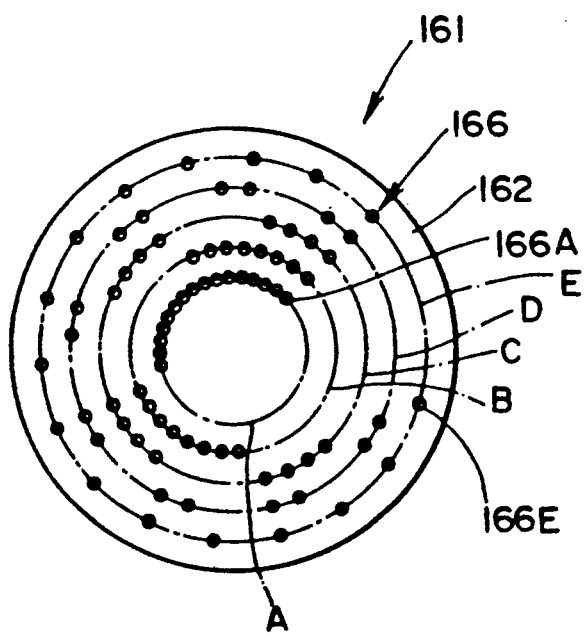

FIGS. 10 and 11 show the third embodiment of the present invention.

In this embodiment, the film exchange detector described in the second embodiment has a counter output function outputting the number of film frames, the cam lever 145 is omitted and an encoder is provided instead of the frame counting plate 135.

An encoder 161 of this embodiment comprises a rotary disc 162, phototransistors 163A, 163B, 163C, 163D and 163E opposed to this rotary disc 162 and provided in the diametral direction of this rotary disc 162 and photodiodes 164A, 164B, 164C, 164D and 164E opposed to the rotary disc 162 and provided on the side reverse to the side on which the phototransistors 163 are provided.

The above mentioned rotary disc 162 is fixed to a shaft 136 so that the number of frames may be increased when a ratchet wheel 134 provided on this shaft 136 is rotated by an engaging pawl 142. In this rotary disc 162, as in FIG. 11, a plurality of holes 166 are made on five concentric circles of different radii. The holes 166 made on the innermost circle A of these concentric circles pass the light emitted from the above mentioned photodiode 164A to enter the phototransistor 163A. The holes 166 made on the circle B positioned outside the circle A pas the light emitted from the above mentioned photodiode 164B to enter the phototransistor 163B. In the following, in the same manner, the photodiode 164C and phototransistor 163C correspond to the circle C positioned outside the circle B and the photodiode 164D and phototransistor 163D correspond to the circle D positioned outside the circle C.

When the lights are detected, the above mentioned phototransistors 163A, 163B, 163C, 163D and 163E will generate electromotive forces and will output electric signals. The output of this phototransistor 163A corresponds to the fifth bit of a binary number, the phototransistor 163B corresponds to the fourth bit, the phototransistor 163C to the third bit, the phototransistor 163D to the second bit and the phototransistor 163E to the first bit. That is to say, in FIG. 11, when one frame of the film is photographed, the rotary disc 162 will rotate, the light emitted from the photodiode 164E will pass through the hole 166E and will enter the phototransistor 163E corresponding to the first bit but the lights emitted from the other photodiodes 164A, 164B, 164C and 164D will be intercepted by the rotary disc 162. As a result, a binary number 00001 is output in the signal transmitting circuit 82. This binary number is delivered to the operating circuit 74 through the signal receiving circuit 83 and is converted to a decimal number in the operating circuit 74. The decimal number is output to the character superimposing circuit 64 and the number of film frames is superimposed on the composite video signal.

When the film is exchanged, as described in the second embodiment, by the energizing coil spring 151, the rotary disc 162 will be returned to the standing-by position, the lights of the transistors 163A, 163B, 163C, 163D and 163E will be intercepted and the non-sensing state will be made. Therefore, the respective phototransistors 163 output binary numbers 00000 to the signal transmitting circuit 82. This signal is input into the operating circuit 74 through the signal receiving circuit 83 and the film exchange is sensed by this signal in this operating circuit. In the operating circuit 74, when the film exchange is sensed, a signal making the film frame number 0 will be output to the character superimposing circuit 64 and the film frame number 0 will be superimposed on the composite video signal.

In this embodiment, no counter is provided but the film exchange detector has a count detecting function and therefore the formation of the photographing apparatus body 226 can be made simple.

The other formations, operations and effects are the same as in the second embodiment.

Figure 12:
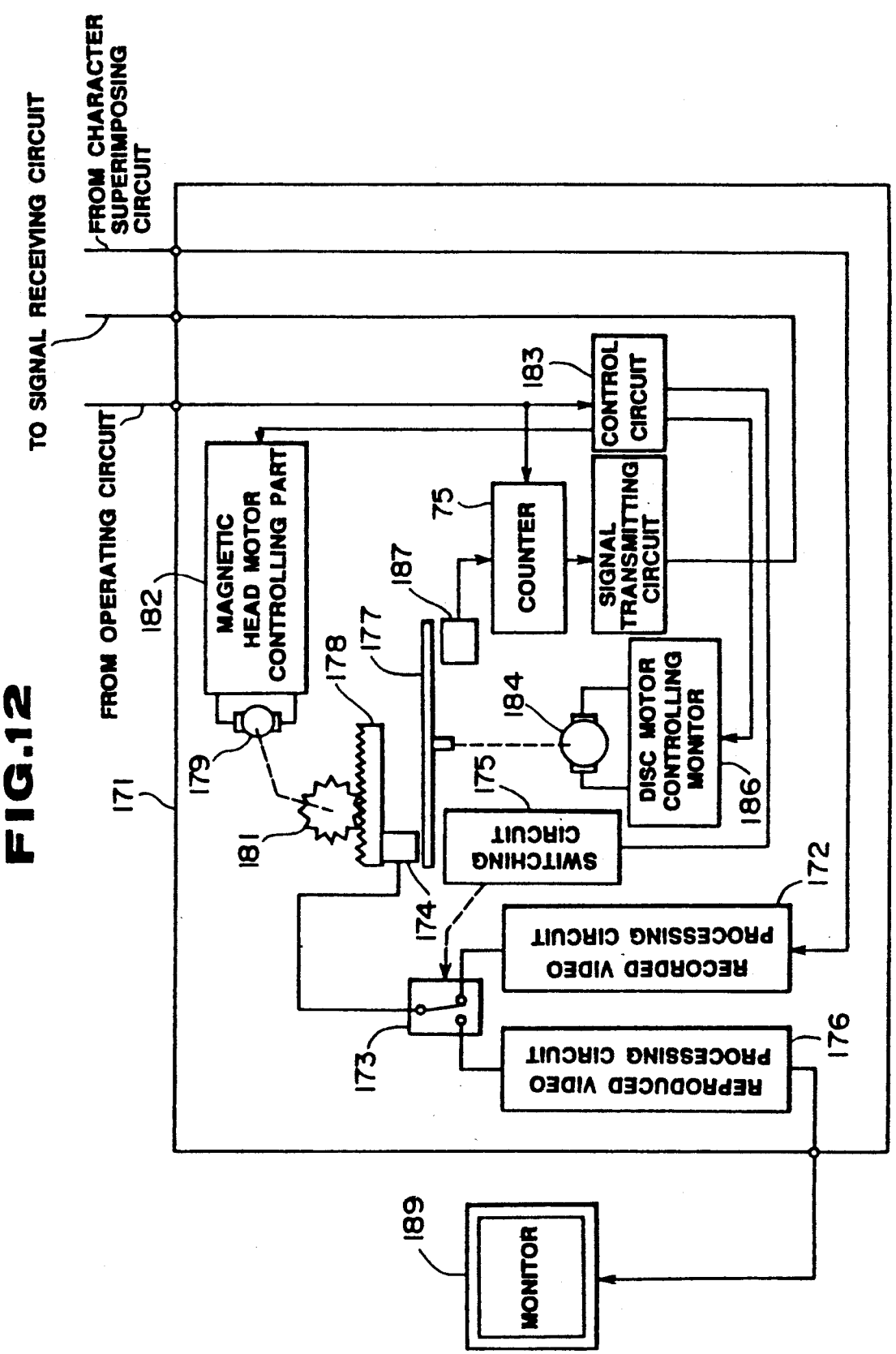
FIG. 12 relates to the fourth embodiment of the present invention and is an explanatory view of the formation of a picture image recording apparatus.

FIG. 12 shows the fourth embodiment of the present invention.

In this embodiment, an endoscope image is output in a magnetic recording and reproducing apparatus.

In this embodiment, a magnetic recording and reproducing apparatus is provided in place of the photographing apparatus body described in the first embodiment and the other formations are the same as in the first embodiment.

A magnetic recording and reproducing apparatus 171 of this embodiment has a recorded video processing circuit 172 receiving an output signal of the character superimposing circuit 64 described in the first embodiment. In this recorded video processing circuit 172, a color signal and luminance signal are taken out of an input composite video signal, the color signal is converted to be in a low frequency range to be a low range converted color signal and the luminance signal is FM-modulated to be an FM luminance signal. Further, the low range converted color signal and FM luminance signal are mixed and are output to a recording and reproducing magnetic head 174 through a switching circuit 173. By the way, the switching circuit 173 consists, for example, of a switching switch which will be switched at the time of reproduction by a switching circuit controlling part 175 so as to be able to output a reproduced video signal coming from the recording and reproducing magnetic head 174 to a reproduced video processing circuit 176.

The above mentioned recording and reproducing magnetic head 174 records the output signal of the above mentioned recorded video processing circuit 172 on the magnetic disc 177 as a recording medium and is provided with a rack 178 meshing with a pinion 181 fitted to a tracking motor 179 so as to be able to track on the magnetic disc 177. The tracking motor 179 is driven by a magnetic head motor controlling part 182 which is connected to a control circuit 183 outputting a control signal controlling the tracking motor by receiving a releasing signal output from the operating circuit 74 described in the first embodiment.

The above mentioned magnetic disc 177 is removably fitted to the driving shaft of a disc motor 184 so as to be rotated by this disc motor 184 controlled in the rotation by a disc motor controlling part 186 into which a control signal is input from the above mentioned control circuit 183.

Such disc exchange detector 187 as, for example, a photocoupler is provided as opposed to the disc surface of the above mentioned magnetic disc 177 so as to output a control signal to the counter 75 in case the magnetic disc 177 is not fitted to the disc motor 184. The releasing signal to be input into the above mentioned control circuit 183 is branched and input into this counter 75 so that the number of inputs of this releasing signal may be integrated. This number of inputs is to be reset by the control signal input from the above mentioned disc exchange detector 187.

The integrated value of the above mentioned counter 75 is transmitted to the signal transmitting circuit 82 and is further delivered to the signal receiving circuit 83 provided within the control apparatus 23.

At the time of the reproduction, the reproduced signal from the recording and reproducing magnetic head 174 through the switching circuit 173 switched by the switching circuit controlling part 175 will be input into the above mentioned reproduced video processing circuit 176 in which the reproduced signal will be FM-demodulated and frequency-converted and a video signal will be output to a reproducing monitor 189 connected to the magnetic recording and reproducing apparatus 171. The video image recorded on the magnetic disc 177 is displayed on the picture surface of the reproduced monitor 189.

The other formations are the same as in the first embodiment.

The operation of the magnetic recording and reproducing apparatus formed as mentioned above shall be explained.

A video signal obtained by the electronic scope 22 and processed by the control apparatus 23 is input into a recorded video processing circuit 172 provided in the magnetic recording and reproducing apparatus 171 through the character superimposing circuit 64. At this time, the switching circuit 173 will be connected by the switching controlling part neither to the recorded video processing circuit 172 side nor to the reproduced video processing circuit 176 side and no recorded video signal will be output in the magnetic head 174.

Here, in the case of recording an endoscope image, a releasing signal will be input into the control circuit 183 and counter 75 within the magnetic recording and reproducing apparatus 171 through the operating circuit 74 from the releasing switch 73 provided in the control apparatus 23. The control circuit 183 outputs a control signal to the magnetic head motor controlling part 182 to drive the tracking motor 179 and moves the magnetic head 174 onto the recording region sectioned on the disc surface of the magnetic disc 177. The control circuit 183 outputs a signal to the switching circuit controlling part 175 to switch the switching circuit 173 and delivers to the magnetic head 174 the recorded video signal processed by the recorded video processing circuit 172. Thus, the recorded video signal is recorded in a predetermined recording region on the magnetic disc 177.

When the recording ends, the control circuit 183 will feed a control signal to the switching circuit controlling part 175 and the switching circuit 173 switched to the recorded video processing circuit 172 side will be connected neither to the recording side nor to the reproducing side.

On the other hand, the counter 75 in which the releasing signals have been input integrates the releasing signals and outputs this integrated value to the signal transmitting circuit 82 which outputs the integrated value. This integrated value is fed to the signal receiving circuit 83 provided within the control apparatus 23 and is input into the operating circuit 74 from this signal receiving circuit. In the operating circuit 74, the number of remaining picture images which can be recorded in the magnetic disc 177 is calculated from this integrated value and the number of remaining picture images is output to the character superimposing circuit 64 in which the number of remaining picture images is superimposed on the composite video signal produced by the video processing circuit 41 and the video signal is output to the observing monitor 24 and recorded video processing circuit 172. In the observing monitor 24, not only the endoscope image but also the number of remaining picture images which can be recorded in the magnetic disc 177 are displayed.

When a releasing signal is input again from the releasing switch 73, the control circuit 183 will again output a control signal to the magnetic head motor controlling part 182 to move the magnetic head 174 on a recording region different from the above mentioned one sectioned on the magnetic disc 177.

Also, when the releasing signal is input, the counter 75 will increase the integrated value and will output this increased integrated value to the control apparatus 23 through the signal transmitting circuit 82.

When the recording is repeated in the same manner in the following until there is no recording region in the magnetic disc 177, the number of remaining picture images will be displayed to be 0 in the observing monitor 24 and the operator will exchange the magnetic disc 177. The disc exchange detector 187 detects the exchange of the magnetic disc 177 and outputs the resetting signal to the counter 75. The counter 75 having received the resetting signal resets the integrated value to be 0 and outputs this value to the control apparatus 23 through the signal transmitting circuit 82. The operating circuit 74 calculates the number of picture images which can be recorded by the magnetic disc 177 and outputs the number to the character superimposing circuit 64.

In case a picture image recorded in the magnetic disc 177 is to be produced, a reproducing signal from a reproducing switch not illustrated and a signal designating the recording region on the magnetic disc 177 are input into the control circuit 183 which controls the magnetic head motor controlling part 182, selects the recording region to be reproduced out of the magnetic disc 177—moves the magnetic head 174, then outputs a control signal to the switching circuit controlling part 175 and delivers to the reproduced video processing circuit 176 the video signal read out of the magnetic head 174. The reproduced video processing circuit 176 makes the FM demodulation and frequency conversion of the video signal, delivers the composite video signal to the reproducing monitor 189 and displays the recorded picture image on this reproducing monitor 189.

As in this embodiment, even in case the disc exchange detector 187 is provided and the magnetic disc 177 is exchanged, the number of the photographed frames on the observing monitor 24 will be reset. Therefore, the magnetic disc 177 is prevented from being exchanged though there is a recording space in the magnetic disc.

Figure 13:
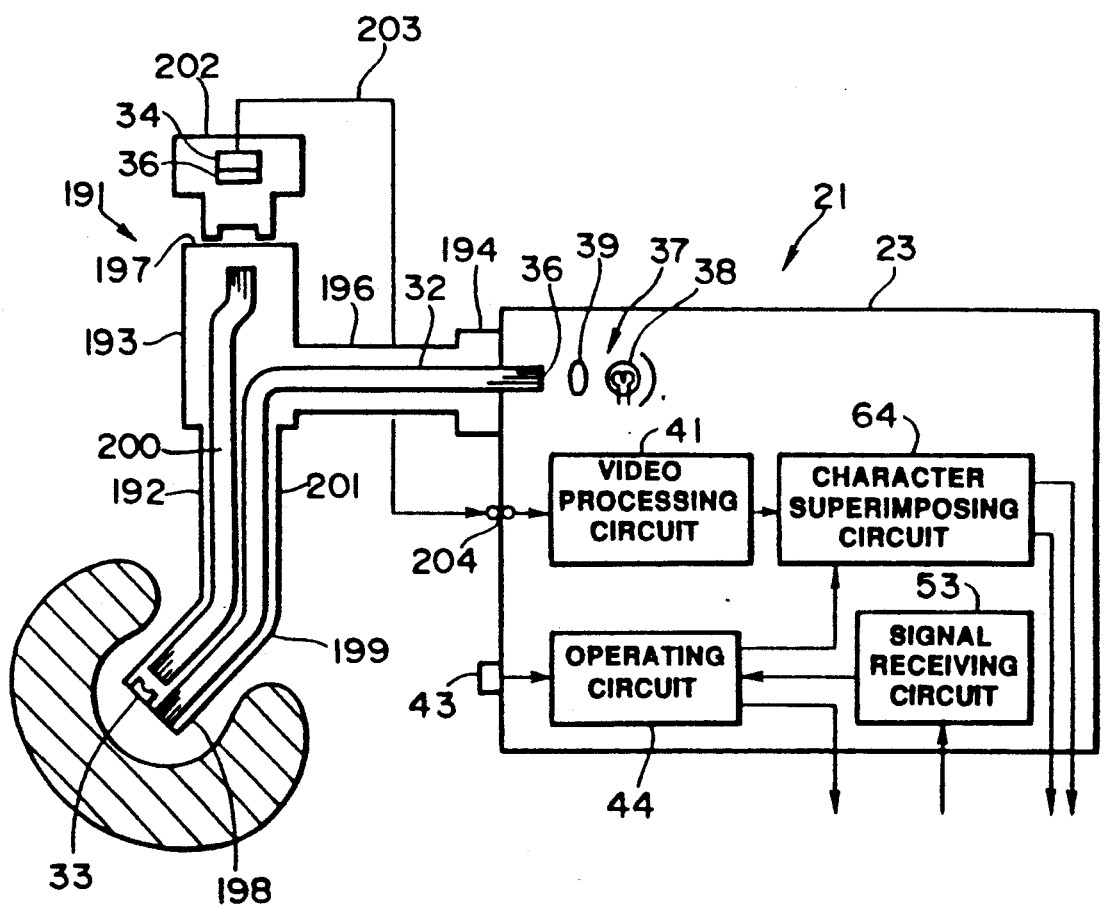
FIG. 13 relates to the fifth embodiment of the present invention and is an explanatory view of an endoscope system as fitted with a TV camera externally fitted to a fiber scope.

FIG. 13 shows the fifth embodiment of the present invention and is an explanatory view of an endoscope system in case a fiber scope is fitted with an externally fitted television camera.

A fiber scope 191 comprises an elongate flexible insertable part 192, a thick operating part 193 provided as connected to this insertable part in the rear, a universal cable 196 extended out of the side of this operating part 193 and provided at the tip with a connector 194 and an eyepiece part 197 provided at the rear end of the above mentioned operating part 193.

The above mentioned insertable part 192 comprises in order from the tip side a tip part 198 having on the tip surface an observing window not illustrated, a curvable part 199 which is provided as connected to this tip part 198 in the rear and can direct this tip part 198 in the vertical and horizontal directions and a flexible part 201 provided as connected to this curvable part 199 in the rear.

The above mentioned insertable part 192 is provided at the tip with the exit end surface of a light guide 32 formed of a fiber bundle inserted through the universal cable 196 and insertable part 192 so as to illuminate an observed part and with an objective lens 33 forming the image of the illuminated observed part on the entrance end surface of an image guide 200 formed of a fiber bundle. This image guide 200 is inserted through the insertable part 192 and operating part 193 and leads to the eyepiece part 197 so that the observed part may be observed with a naked eye from this eyepiece part 197.

An externally fitted television (TV) camera 202 is connected to the above mentioned eyepiece part 197 so that the image of the observed part transmitted through the above mentioned image guide 200 may be formed on a solid state imaging device 34 provided within this externally fitted TV camera 202. By the way, a color filter array 36 provided in the form of a mosaic with color separating filters transmitting respective colors, for example, of R(red), G(green) and B(blue) is pasted on the imaging surface of the solid state imaging device 34. A signal cable 203 delivering a picture image signal obtained by photoelectrically converting the image formed on the solid state imaging device 34 is extended from the externally fitted TV camera 202. The signal connector 204 provided at the tip of this signal cable 203 is connected to a control apparatus 23 so that the picture image signal may be output to a video processing circuit 41 provided within a control apparatus 23.

The control apparatus 23 has a light source lamp 38 emitting an illuminating light and a condenser lens 39 condensing this illuminating light so that the illuminating light condensed by this condenser lens 39 may be radiated onto the entrance end surface of the light guide 32 provided in the above mentionend connector 194.

The other formations and operations are the same as in the first embodiment.

Figure 14:
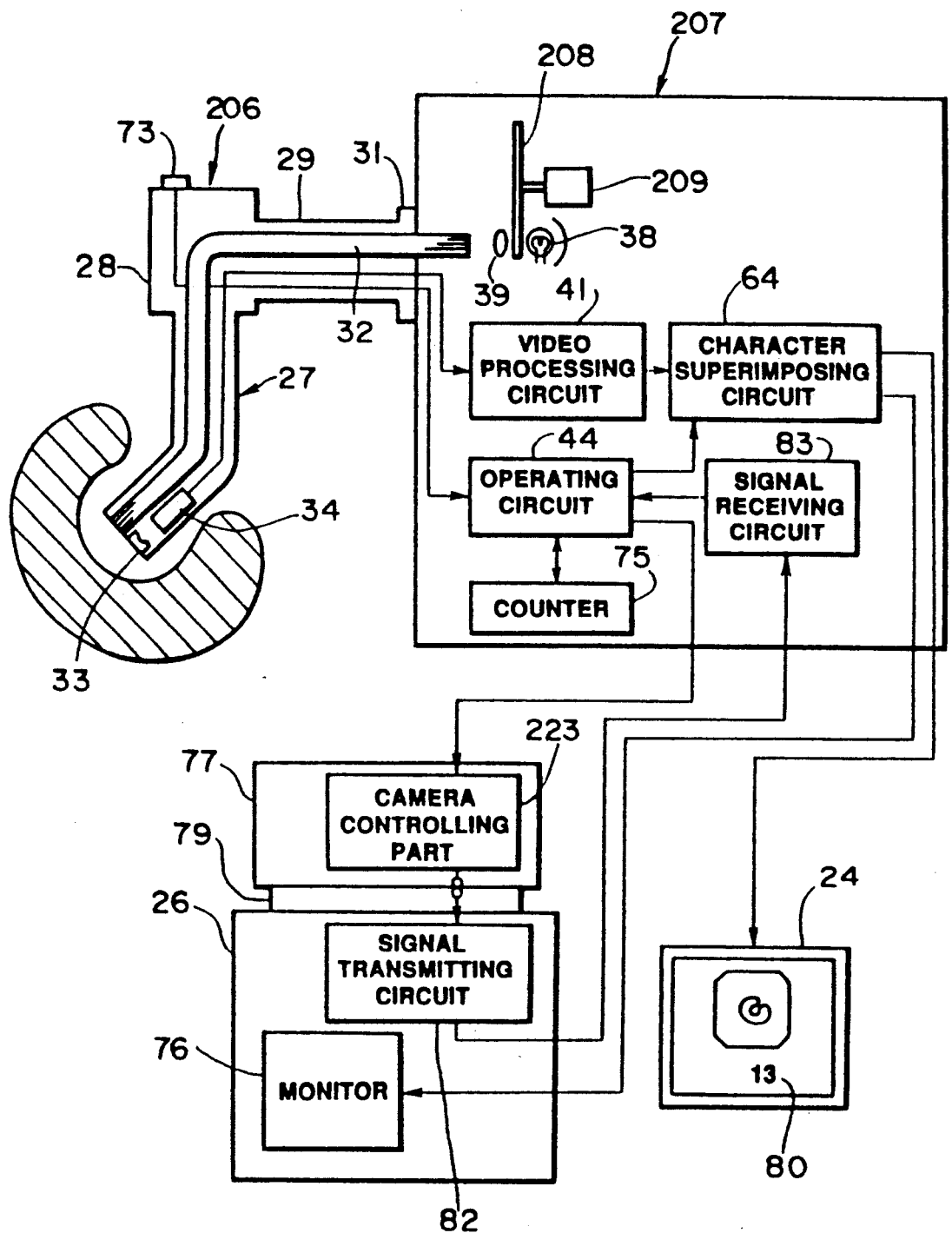
FIGS. 14 and 15 relate to the sixth embodiment of the present invention.
Figure 15:
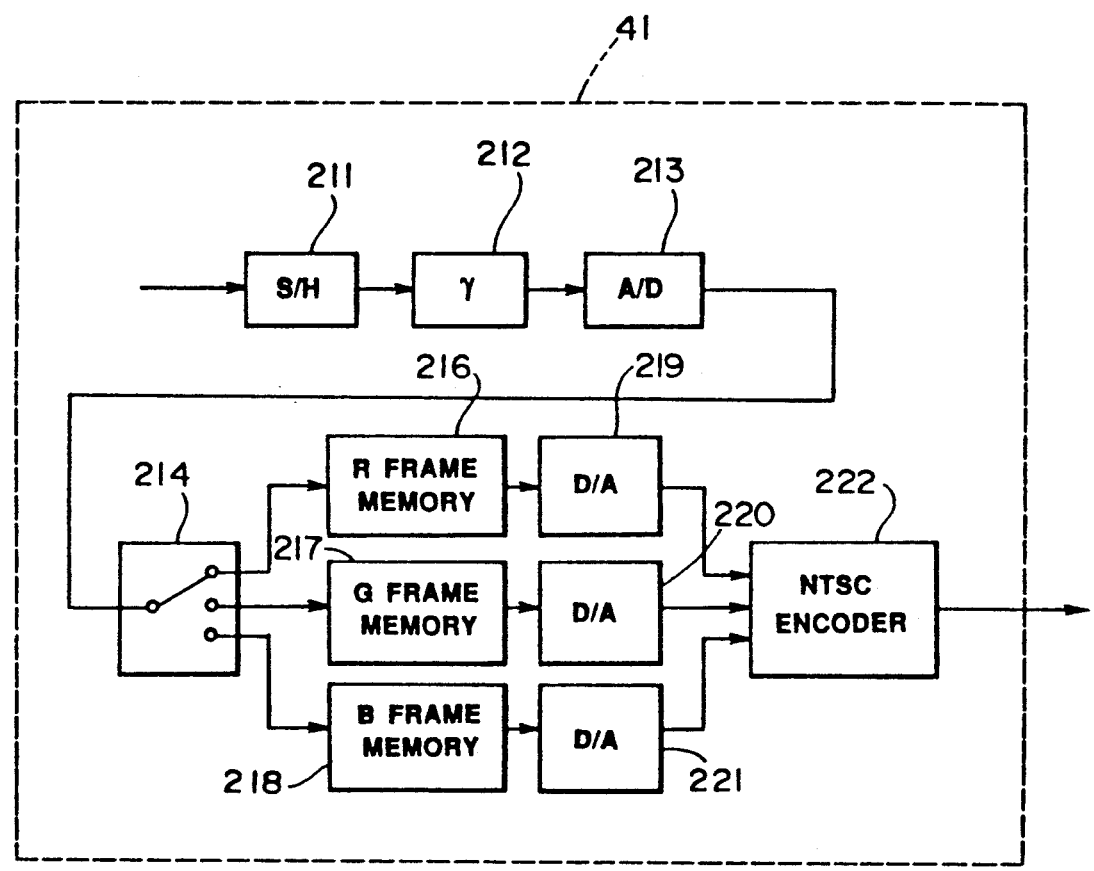

FIGS. 14 and 15 show the sixth embodiment of the present invention.

In the endoscope apparatus of this embodiment, the imaging system is made a frame sequential system.

As compared with the first embodiment, in this embodiment, the electronic scope 206 has no color filter array 36 on the imaging surface of the solid state imaging device 34 and the operating part 28 is provided at the rear end with a releasing switch 73. The others are the same as of the electronic scope 22 described in the first embodiment.

Also, as compared with the first embodiment, a control apparatus 207 is provided with a rotary filter 209 in the light source part and further a counter 75 counting the number of film frames is provided. The others are the same as in the first embodiment.

The above mentioned rotary filter 208 is provided in the peripheral direction with color transmitting filters transmitting respective colors, for example, of R(red), G(green) and B(blue) so as to be rotated by a motor 209 and interposed in time series between the light source lamp 38 and condenser lens 39 to separate the illuminating light into respective color lights.

As compared with the first embodiment, a photographing apparatus body 26 does not have a film exchange detector and a counter but has a camera controlling part 223 described in the second embodiment. This camera controlling part 223 photographs the image of the photographing monitor 76 and outputs to a signal transmitting circuit 82 a signal representing the film exchange in case the film is exchanged. This signal transmitting circuit 82 delivers this film exchange signal to an operating circuit 74 through a signal receiving circuit 83.

The operation of this embodiment shall be explained.

An illuminating light having had the colors separated by the rotary filter 208 is transmitted through the light guide 32 and is emitted to an observed part from the tip of the insertable part 27. The images corresponding to the respective color lights of red, green and blue of the illuminated observed part are formed on the imaging surface of the solid state imaging device 34. These images are photoelectrically converted and are delivered as an electric signal to a video processing circuit 41 within the control apparatus 23.

In FIG. 15, the electric signal from the solid state imaging device 34 has the video signal extracted in a sample holding circuit 211, has γ corrected in a γ-correcting circuit and then is converted to a digital signal in an A/D converter 213. This electric signal is repeated as synchronized with a color frame sequential illumination by a multiplexer 214 and is sequentially memorized in an R frame memory 216, G frame memory 217 and B frame memory 218 corresponding to the respective colors of red, green and blue. The signals of the above mentioned respective frame memories 216, 217 and 218 are simultaneously read out in the lateral direction at a speed matching the monitors 24 and 76, are converted to analog signals respectively by D/A converters 219, 220 and 221 to be R, G and B color signals. These R, G and B color signals are converted to a composite video signal of an NTSC system by an NTSC encoder 222.

The composite video signal of the NTSC system produced as mentioned above is delivered to a character superimposing circuit 64, has the number of film frames superimposed and is output to the observing monitor 24 and photographing monitor 76. An endoscope image having had the number of film frames superimposed is displayed in the observing monitor 24 and photographing monitor 76.

In the case of photographing the endoscope image, a releasing signal is input into an operating circuit 74 from the releasing switch 73 provided on the operating part 28. The operating circuit 74 receives the releasing signal, instructs the counter 75 to count up the film frames and simultaneously outputs to the character superimposing circuit 64 the counted value as a number of film frames and the monitors 24 and 76 display the picture image on which the counted number of film frames is displayed. Further, the operating circuit 74 outputs a releasing signal to the camera controlling part 223 provided on the photographing apparatus body 26 to photograph the picture image of the photographing monitor 76.

In the case of exchanging the film, as described in the second embodiment, the leader part feeding ② from the releasing ① of the back lid 91 of the camera 77 is detected by the first to third photocouplers 139, 149 and 150 to detect the film exchange and this detecting signal is output to the signal transmitting circuit 82 and is delivered to the operating circuit 74 through the signal receiving circuit 83. The operating circuit 74 resets the integrated value of the counter 75 to be 0 with the detecting signal and outputs this numerical value 0 to the character superimposing circuit 64.

Thereafter, the same as in the first embodiment, the reset number 80 of film frames is displayed on the picture surfaces of the monitors 24 and 76.

In this embodiment, as the camera controlling part 223 has a function of detecting the film exchange, the film exchange detector can be omitted and further, as the control apparatus 23 is provided with the counter 75, the photographing apparatus body 26 can be made small.

The other formations, operations and effects are the same as in the first embodiment.

Figure 16:
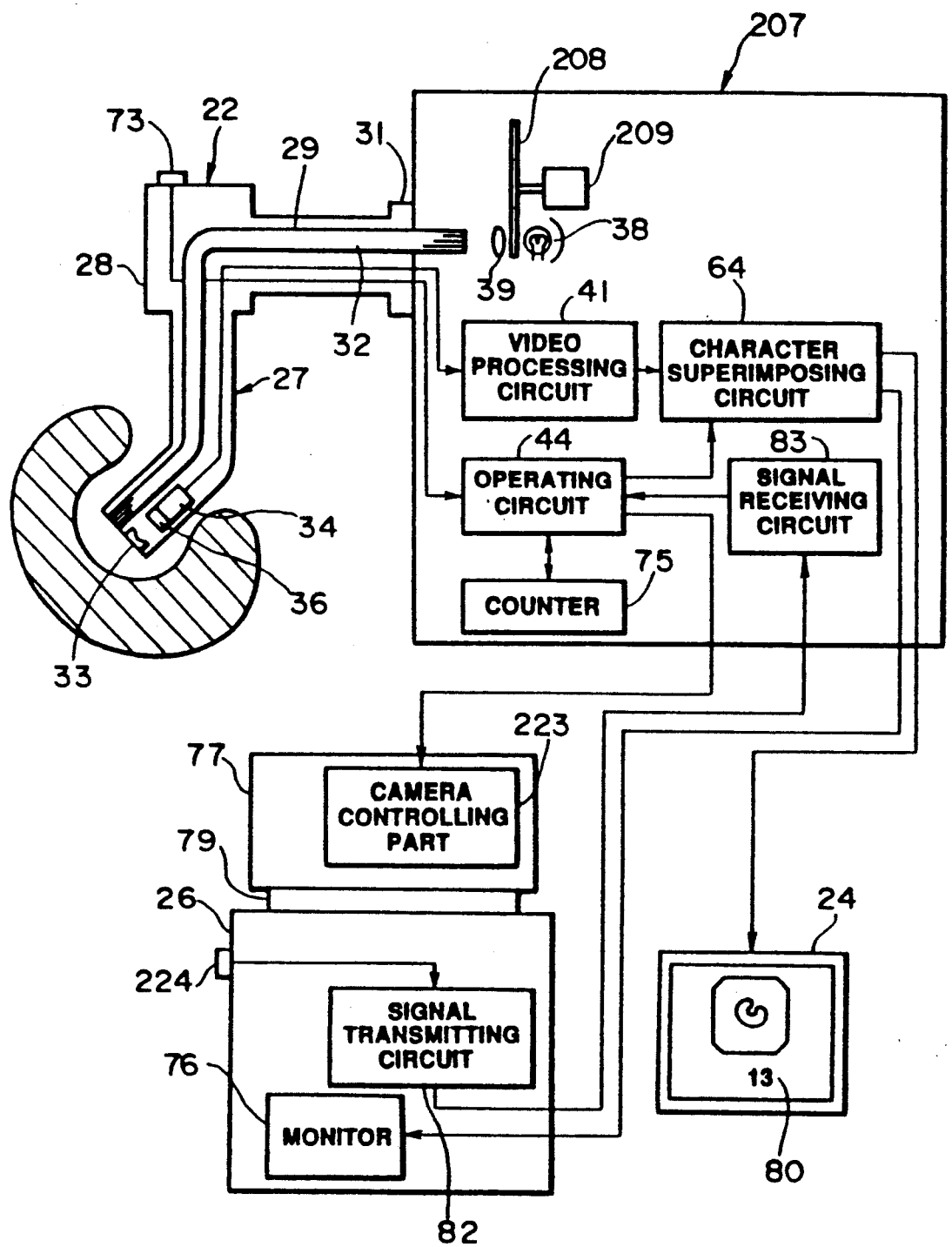
FIG. 16 relates to the seventh embodiment of the present invention and is an explanatory view of an endoscope system having a resetting switch in a photographing apparatus.

FIG. 16 shows the seventh embodiment of the present invention.

In this embodiment, instead of a film exchange sensing signal delivered to the signal transmitting circuit 82 from the camera controlling part 223 in the sixth embodiment, the photographing apparatus body 26 is provided with a resetting switch resetting the number of film frames. The other formations are the same as in the sixth embodiment.

The operation of this embodiment shall be explained.

The camera controlling part 223 photographs the picture image of the photographing monitor 76 with a releasing signal from the operating circuit 74. This camera controlling part 223 does not output such film exchange detecting signal as in the sixth embodiment. In the case of exchanging the film, after the film is exchanged, the operator operates a resetting switch 224 which is a manual switch provided on the photographing apparatus body 26. The resetting switch 224 delivers a resetting signal to the signal transmitting circuit 82 which delivers the resetting signal to the operating circuit 74 through the signal receiving circuit 83.

Thereafter, the same as in the sixth embodiment, the signal is processed and the displayed number 80 of the film frames displayed in the monitors 24 and 76 is reset to be 0.

In this embodiment, as the film exchange detecting signal is input by operating the resetting switch, no special mechanism for detecting the film exchange is required and the camera controlling part 223 can be simplified.

The other formations, operations and effects are the same as in the first embodiment.

Figure 17:
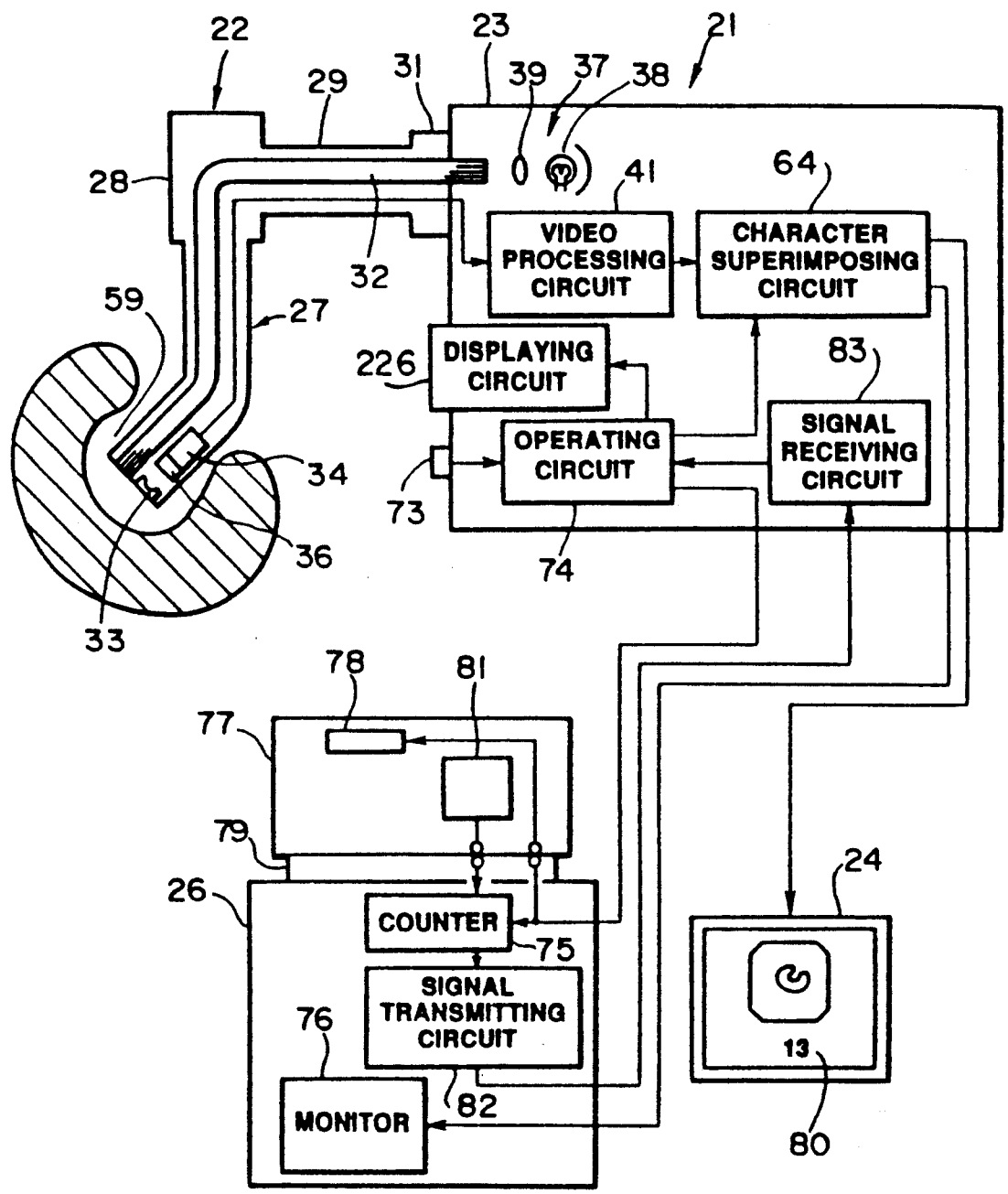
FIG. 17 relates to the eighth embodiment of the present invention and is an explanatory view of an endoscope system having a displaying circuit in a control apparatus.

FIG. 17 shows the eighth embodiment of the present invention.

In this embodiment, the control apparatus described in the first embodiment is provided with a displaying circuit displaying the number of film frames.

The other formations are the same as in the first embodiment.

In this embodiment, the number of film frames output to a character superimposing circuit 64 from an operating circuit is output also to a displaying circuit 226 which has such displaying part as, for example, of a liquid crystal displaying the number of film frames.

In this embodiment, as the number of film frames is displayed not only on the picture surfaces of the monitors 24 and 76 but also by the control apparatus 23, for example, even in the case of inspecting the number of remaining frames before using the endoscope system, even if the number of film frames is not displayed in the observing monitor 24 by operating the entire system, the number of remaining frames can be easily inspected from the displaying part. Therefore, the operatability of the endoscope system can be improved.

The other operations and effects are the same as in the first embodiment.

Figure 18:
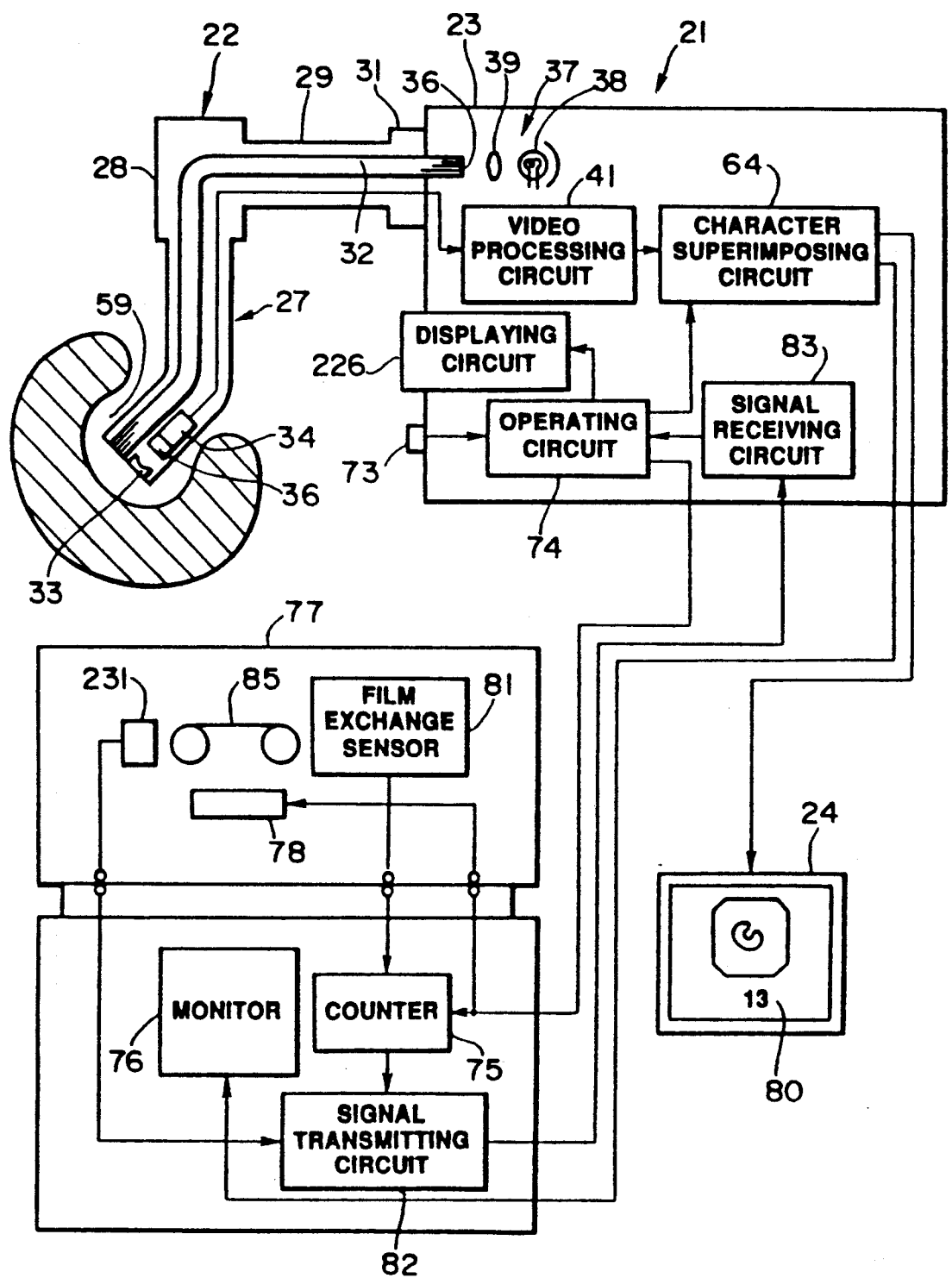
Figure 19A:
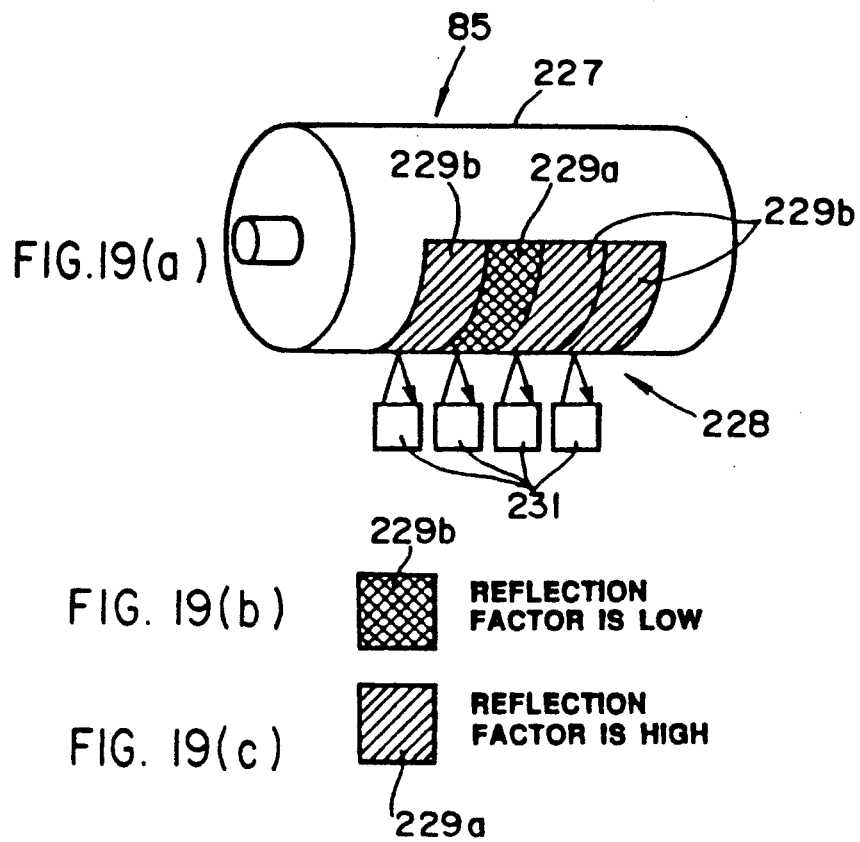
Figure 20:
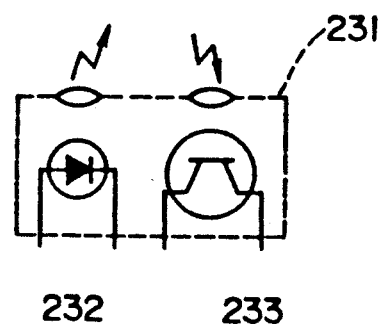

FIGS. 18 to 20 show the ninth embodiment of the present invention.

In this embodiment, the camera of the eighth embodiment is provided with photosensors detecting the kind of the film. The other formations are the same as in the eighth embodiment.

A cartridge 227 of a film 85 to be fitted to a camera 77 is provided on the outer peripheral surface with such mark 228 as is shown in FIG. 19. This mark 228 is formed, for example, of four band-like reflecting members 229 of different reflection factors. The reflecting member 229a is high in the reflection factor but the reflecting members 229b are low in the reflection factor. For example, four reflecting type photosensors 231 are provided as opposed to these four reflecting members 229. One reflecting type photosensor 231 is provided with a photodiode 232 and phototransistor 233 in a pair as in FIG. 20 so that infrared rays output from the photodiode 232 and reflected by the reflecting member 229 may be received by the phototransistor 233 to discriminate the reflection factor as to whether it is high or low.

In this embodiment, as the four reflecting members 229 are made of two kinds high and low in the reflection factor, 16 kinds of films can be discriminated.

By the way, the number of the reflecting members 229 is not limited to be four. If the kinds of films can be represented, the number of the reflecting members will not be limited.

The mark 228 is formed of members different in the reflection factor but may be formed of reflecting members and not reflecting members.

The above mentioned reflecting type photosensor 231 outputs to a signal transmitting circuit 82 a signal representing the kind of the film. The signal transmitting circuit 82 outputs to a control apparatus 23 a film frame number signal from a counter 75 and a signal representing the kind of the film. In the control apparatus 23, the film frame number signal and the signal representing the kind of the film are input into an operating circuit 74 through a signal receiving circuit 83. In the operating circuit 74, the number of film frames is output to a character superimposing circuit 64 and is superimposed on a composite video signal output from a video processing circuit 41. Also, the number of film frames and the kind of the film are output to the displaying circuit 226 described in the eighth embodiment and are displayed in a displaying part not illustrated.

The operation of this embodiment shall be explained.

Displaying the number of film frames of the monitors 24 and 76 and resetting the number of film frames at the time of exchanging the film are the same as in the first embodiment.

Further, in the case of exchanging the film, the mark 228 representing the kind of the film and provided on the cartridge 227 is read up by the reflectng type photosensor 231 provided within the camera 77. The reflecting type photosensor 231 outputs, for example, "1" in the case of the reflecting member 229a high in the reflection factor and "0" in the case of the reflecting member 229b low in the reflection factor and outputs to the signal transmitting circuit 82 a binary number 1011 representing the kind of the film. The signal transmitting circuit 82 outputs a film frame number signal input from the counter 75 and a binary number 10 representing the kind of the film to the operating circuit 74 through the signal receiving circuit 83. In the operating circuit 74, the film frame number signal is output to the character superimposing circuit 64 and displaying circuit 226, a binary number 1011 representing the kind of the film is decoded and the kind of the film is output to the displaying circuit 226. Thereby, the number of film frames is superimposed on the composite video signal in the character superimposing circuit 64 and the number of film frames and the kind of the film are displayed in the displaying part not illustrated.

By the way, in the displaying part, only the kind of the film may be displayed or the data other than the kind of the film may be displayed.

In this embodiment, as the kind of the film 85 is displayed in the control apparatus 23, even after the film 85 is fitted and the back lid of the camera 77 is closed, the kind of the film 85 can be easily confirmed. Therefore, the film 85 of a different kind can be prevented from being fitted and not only the number of the film frames can be counted and displayed but also such warning as sounding a buzzer can be made when the number of the remaining frames becomes below a fixed value.

The other effects are the same as in the first embodiment.

Figure 21:
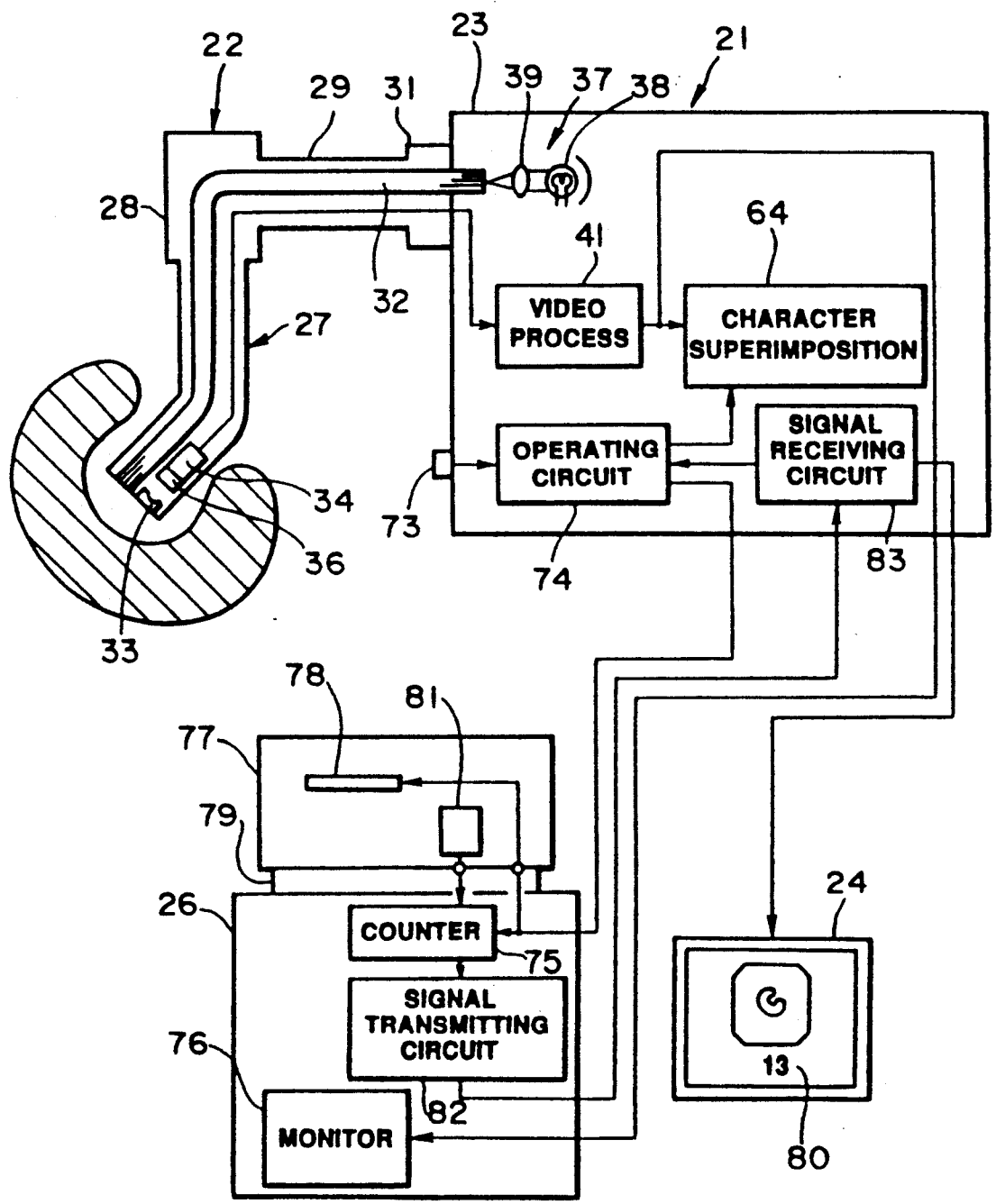
FIG. 21 relates to the tenth embodiment of the present invention and is an explanatory view of an endoscope system in which no character is superimposed on a picture surface of a photographing monitor.
Figure 22:
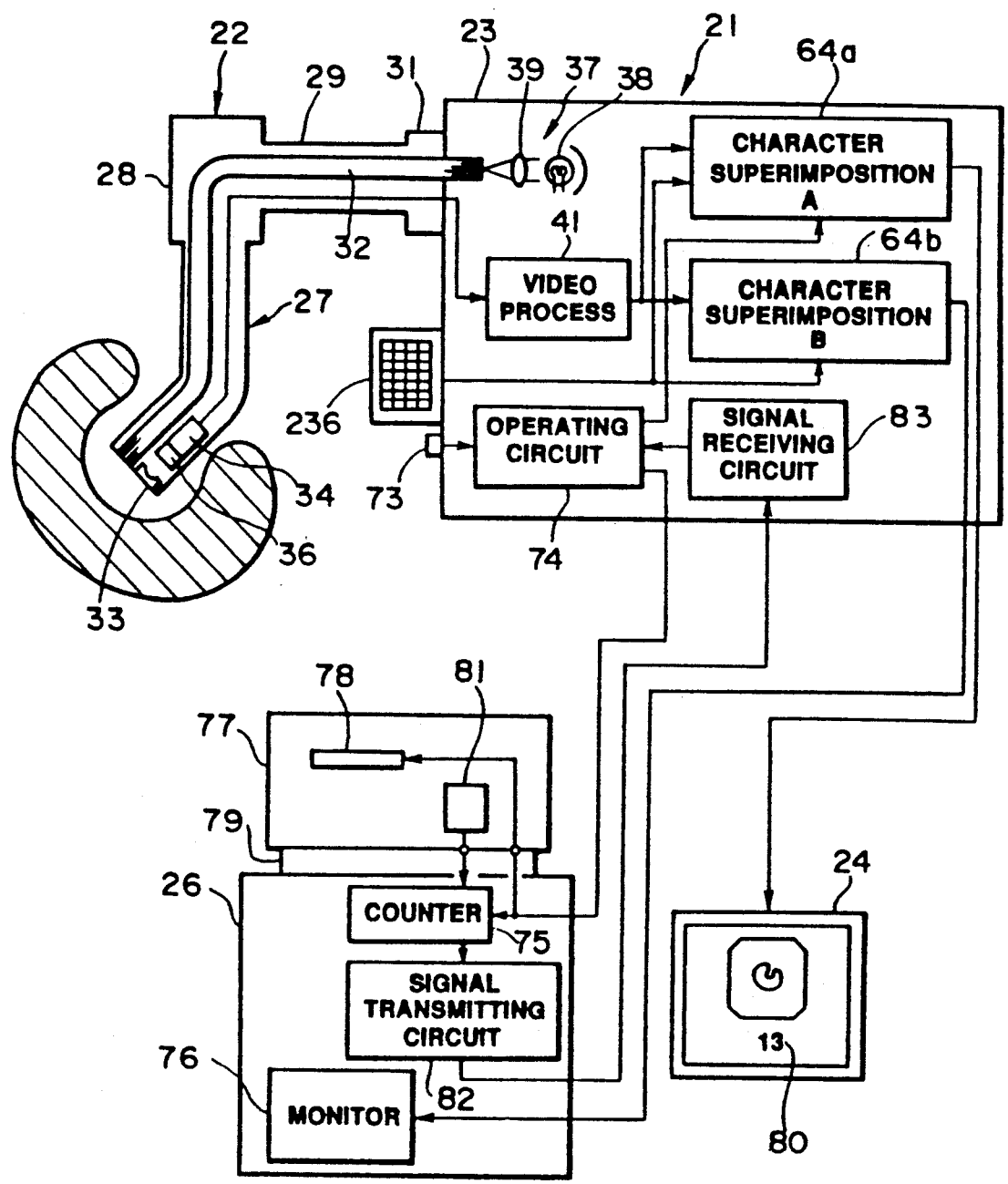

FIG. 21 shows the tenth embodiment of the present invention.

This embodiment is the same as the first embodiment except that the output of the character superimposing circuit is delivered to the observing monitor, the output of the video processing circuit is delivered to the photographing monitor and the number of film frames is displayed only in the observing monitor 24.

A video processing circuit 41 within a control apparatus 23 produces and outputs a composite video signal which is branched and output to a character superimposing circuit 64 and a photographing monitor 76 provided within a photographing apparatus body 26. Only an object image is displayed on the picture surface of this photographing monitor 76.

The above mentioned character superimposing circuit 64 is connected with an operating circuit 74 and the character data not required to be displayed in the photographing monitor 76 are superimposed on the composite video signal. This character superimposing circuit 64 outputs to the observing monitor 24 a composite video signal on which the number of film frames is superimposed and can display on the picture surface of the observing monitor 24 the observed picture image having the display 80 of the number of film frames.

The other formations and operations are the same as in the first embodiment.

By the formation as in this embodiment, in the photographing monitor 76, only the object image is displayed but the number of film frames as character data not required to be displayed in the photographing monitor 76 is not displayed. Therefore, only the object image required as a record photograph can be photographed.

FIGS. 22 to 25 show the 11th embodiment of the present invention.

In this embodiment, an object image and informations relating to a patient input from an external input apparatus are displayed in a photographing monitor 76 and a picture image displayed in the photographing monitor 76 and, in addition, the number of film frames as character data not required to be displayed in the photographing monitor 76 are displayed in the observing monitor 24.

The output of a video processing circuit 41 provided within a control apparatus 23 forming an endoscope system 21 is branched and delivered to a character superimposing circuit A 64a and character superimposing circuit B 64b. Such information relating to a patient as, for example, the ID code, initial, sex, date of birth and other comments of the patient are inpput into these character superimposing circuits A 64a and B 64b from a keyboard 236 as an external input apparatus. In the character superimposing circuit B 64b, the information relating to the patient are superimposed on the video signal input from the video processing circuit 41 and are output to the photographing monitor 76 within a photographing apparatus body 26. Not only the object image but also the information relating to the patient input from the keyboard 236 are displayed on the picture surface of this photographing monitor 76.

On the other hand, in the character superimposing circuit A 64a, not only the information relating to the patient but also the number of film frames from the operating circuit 74 are input and the informations relating to the patient and the number of film frames ar superimposed on the video signal. This superimposed video signal is output to the observing monitor 24 and displays such picture image as is shown in FIG. 25. On the picture surface of this observing monitor 24, for example, the information (such as the ID code and initial of the patient) 238 relating to the patient are displayed on the upper left of the endoscope image 237 and further the number 80 of film frames is displayed below the endoscope image 237. This number of film frames will be renewed when the releasing switch 73 is pushed and will be reset to be 0 when the film 85 is exchanged.

By the formation as mentioned above, the object image, the information relating to the patient and, for example, the number of remaining frames of the film 85 can be displayed in the observing monitor 24, the object image and the informations 238 relating to the patient can be displayed in the photographing monitor 76 and therefore the object image and the informations relating to the patient are recorded in the photograph.

The other formations, operations and effects are the same as in the first embodiment.

By the way, the circuit examples of the character superimposing circuits A 64a and B 64b are shown in FIG. 23.

The character data input from the keyboard 236 are fed to EX.OR gates 239a, 239b and 239c at the first input ends. Color selecting switches 241a, 241b and 241c of color signals R, G and B are connected to the EX.OR gates 239a, 239b and 239c at the second input ends and a background signal of a predetermined voltage is input into the EX.OR gates 239a, 239b and 239c at the second input ends. The outputs of the EX.OR gates 239a, 239b and 239c are input into potentiometers 242a, 242b and 242c and the outputs of the potentiometers 242a, 242b and 242c are input into adders 243a, 243b and 243c and are added to the video signals R, G and B.

According to this circuit, when the color selecting switches 241a, 241b and 241c are off and such character data as are shown in FIG. 24(a) are input into the EX.OR gates 239a, 239b and 239c, an exclusive logical sum operation will be made by the EX.OR gates 239a, 239b and 239c and then the character data will be superimposed on the color signals R, G and B output to the adders 234a, 234b and 234c. These color signal R, G and B are output to the observing monitor 24 or photographing monitor 466. Also, by switching on one or more of the color selecting switches 241a, 241b and 241c, the color of the background can be changed. Further, if the ratio of the colors is varied by adjusting the output voltages of the potentiometers 242a, 242b and 242c, the colors can be freely varied.

Further, the character background can be colored in a color different from that of the characters so that the characters may be easy to see. That is to say, for such character data as are shown in FIG. 24(a), by switching on one or more of the color selecting switches 241a, 241b and 241c, such background signal as is shown in FIG. 24(b) is input into the EX.OR gates 239a, 239b and 239c, an exclusive logical sum operation is made between the character data of FIG. 24(a) and the background signal of FIG. 24(b) and such signal having pulses only in the character background as is shown in FIG. 24(c) is obtained. If the display is made on the basis of the signal shown in this FIG. 24(c), the character background part can be displayed in a color different from that of the character part on the monitor.

In the above mentioned respective embodiment, the control apparatus has the light source part but may be a separate case. Further, the photographing apparatus is a separate case but may be made integral with the control apparatus.

In case the number of frames of the film fitted to the camera is set in the operating circuit and the number of the photographed frames becomes this set number, the end of the film may be displayed on the picture surface of the observing monitor.

As explained above, according to the present invention, there can be provided an endoscope system wherein the state of the photographing apparatus can be known on the observing monitor side by sensing the state of the recording medium, the mis-operation of the photographing apparatus can be prevented and the operability is high.

What is claimed is:

1. An endoscope picture image photographing apparatus comprising:
    a displaying means for displaying as a picture image an observed image obtained by an endoscope;
    a still camera for recording in a recording medium the picture image displayed by said display means; and
    a recording medium state sensing means for sensing the state of said recording medium and externally outputting a signal representing one of a plurality of states of the recording medium, wherein one of said states includes a reset state.

2. An endoscope picture image photographing apparatus according to claim 1 wherein said recording medium is a photographic film.

3. An endoscope picture image photographing apparatus according to claim 1 wherein said recording medium state sensing means is an encoder which is simultaneously a counting means and and is operated by winding up the film.

4. An endoscope picture image photographing apparatus, comprising:
    a displaying means for displaying as a picture image an observed image obtained by an endoscope;
    a still camera for recording in a recording medium the picture image displayed by said displaying means; and
    a recording medium state sensing means for sensing the state of said recording medium and externally outputting a signal representing the state of the recording medium, wherein said recording medium state sensing means consists of a sensor detecting the opening and closing of a lid of the still camera.

5. An endoscope picture image photographing apparatus according to claim 4 wherein said recording medium state sensing means has further a sensor reading a discriminating mark provided on a cartridge of the film.

6. An endoscope picture image photographing apparatus comprising:
    a displaying means for displaying as a picture image an observed image obtained by an endoscope;
    a still camera for recording in a recording medium the picture image displayed by said displaying means; and
    a recording medium state sensing means for sensing the state of said recording medium and externally outputting a signal representing the state of the recording medium, wherein said recording medium state sensing means consists of a sensor sensing a cam rocked by the opening and closing of the lid of the still camera.

7. An endoscope picture image photographing apparatus, comprising:
    a displaying means for displaying as a picture image an observed image obtained by an endoscope;
    a still camera for recording in a recording medium the picture image displayed by said displaying means; and
    a recording medium state sensing means for sensing the state of said recording medium and externally outputting a signal representing the state of the recording medium, wherein said recording medium state sensing means is a resetting switch.

8. An endoscope system, including a picture image photographing apparatus, comprising:
    a control apparatus electrically converting an object image and processing an electric signal obtained by this electric conversion to produce a video signal;
    an observing monitor receiving the video signal output by said control apparatus and displaying as picture images both of the object image and data regarding the state of the picture image photographing apparatus;
    a video recording apparatus receiving the video signal output by said control apparatus and recording said video signal; and
    said control apparatus having a superimposing circuit superimposing data on the video signal and outputting the video signal on which the data have been superimposed in this superimposing circuit and the video signal before the superimposition is made.

9. An endoscope system according to claim 8 wherein the video signals before and after the superimposition are simultaneously output.

10. An endoscope system according to claim 8 wherein at least one of the video recording apparatus and observing monitor is formed to be integral with the control apparatus.

11. An endoscope system according to any of claims 8 and 10 wherein said control apparatus outputs to said observing monitor the video signal after the superimposition is made and to said video recording apparatus the video signal before the superimposition is made.

12. An endoscope system comprising:
    an imaging means inserted into an observed object part, for outputting as a picture image signal through an objective optical system the image of the observed part illuminated by an illuminating optical system, said imaging means including an optical endoscope having an image guide means transmitting to an eyepiece part the observed image by the objective optical system and a television camera fittable to said eyepiece part and imaging the observed image;
    a signal processing means for processing and displaying in a monitor the picture image signal output by said imaging means;
    a recording means for recording in a recording medium the picture image displayed in the monitor by said signal processing means;
    a counting means for counting the record amount of said recording means with a releasing signal input; and
    a recording medium state sensing means for detecting the state of the recording medium of said recording means and resetting the record amount counted by said counting means.

13. An endoscope system according to claim 12 wherein said signal processing means has a superimposing circuit for superimposing on a video signal a signal representing a record amount obtained from said counting means and displaying in said monitor both of the record amount and observed image.

14. An endoscope system according to claim 13 wherein said signal processing means is further provided with said counting means.

15. An endoscope system according to claim 13 wherein said signal processing means has further a displaying means for receiving and displaying the record amount from said counting means.

16. An endoscope system according to claim 13 wherein said signal processing means has further a displaying means displaying the record amount from said counting means and the kind of the film.

17. An endoscope system according to claim 13 wherein said signal processing means further outputs to said recording means the video signal before the superimposition is made by said superimposing means.

18. An endoscope system according to claim 12 wherein said signal processing means has a first superimposing circuit, a second superimposing circuit and a data input means, said first superimposing circuit superimposes on the video signal and outputs to said monitor the data input from said data input means and the record amount input from said counting means and said second superimposing circuit superimposes on the video signal and outputs to said recording means the data input from said data input means.

19. An endoscope system comprising:
   an imaging means inserted into an observed object part, for outputting as a picture image signal through an objective optical system the image of the observed part illuminated by an illuminating optical system;
   a signal processing means for processing and displaying in a monitor the picture image signal output by said imaging means;
   a still camera for recording in a recording medium the picture image displayed in the monitor by said signal processing means;
   a counting means for counting the record amount of said still camera with a releasing signal input; and
   a recording medium state sensing means for detecting the state of the recording medium of said still camera and resetting the record amount counted by said counting means.

20. An endoscope system according to claim 19 wherein aid recording medium is a photographic film.

21. An endoscope system according to claim 19 wherein said recording medium state sensing means consists of a sensor sensing a cam rocked by the opening and closing of the lid of the still camera.

22. An endoscope system according to claim 19 wherein said recording medium state sensing means is an encoder which is simultaneously a counting means and is operated by winding up the film.

23. An endoscope system according to claim 19 wherein said recording medium state sensing means is a resetting switch.

24. An endoscope system according to claim 19 wherein said imaging means comprises an electronic endoscope having a releasing switch capable of making recording.

25. An endoscope system according to claim 19 wherein said still camera has a releasing switch capable of a making recording.

26. An endoscope system according to claim 19 wherein said recording medium state sensing means consists of a sensor detecting the opening and closing of the lid of the still camera.

27. An endoscope system according to claim 26 wherein said recording medium state sensing means has further a sensor reading a discriminating mark provided on a cartridge of the film.

* * * * *